US007239731B1

(12) United States Patent
Semenov et al.

(10) Patent No.: US 7,239,731 B1
(45) Date of Patent: Jul. 3, 2007

(54) SYSTEM AND METHOD FOR NON-DESTRUCTIVE FUNCTIONAL IMAGING AND MAPPING OF ELECTRICAL EXCITATION OF BIOLOGICAL TISSUES USING ELECTROMAGNETIC FIELD TOMOGRAPHY AND SPECTROSCOPY

(75) Inventors: Serguei Y. Semenov, Charlotte, NC (US); Yuri E. Sizov, Troitsk (RU); Alexander E. Bulyshev, Charlotte, NC (US); Alexander E. Souvorov, Germantown, MD (US); Vitaly G. Posukh, Charlotte, NC (US)

(73) Assignee: EMImaging Ltd, Greenwich, London (GB)

( * ) Notice: Subject to any disclaimer, the term of this patent is extended or adjusted under 35 U.S.C. 154(b) by 688 days.

(21) Appl. No.: 10/724,448

(22) Filed: Nov. 26, 2003

Related U.S. Application Data

(60) Provisional application No. 60/429,272, filed on Nov. 26, 2002.

(51) Int. Cl.
*G06K 9/00* (2006.01)

(52) U.S. Cl. ...................................... 382/128; 600/425

(58) Field of Classification Search ................ 382/128, 382/129, 130, 131, 132, 133, 134; 600/2, 600/10, 13, 407, 425, 429, 430, 493, 494, 600/506, 509, 512–514, 536, 537, 546, 547; 128/203.17, 203.27, 204.21, 901, 905, 908; 324/637, 638, 639; 606/27, 32–34; 607/89, 607/101; 73/601, 602, 620

See application file for complete search history.

(56) References Cited

U.S. PATENT DOCUMENTS

| | | | | |
|---|---|---|---|---|
| 5,715,819 | A * | 2/1998 | Svenson et al. | 600/425 |
| 6,026,173 | A * | 2/2000 | Svenson et al. | 382/131 |
| 6,333,087 | B1 | 12/2001 | Jerdee et al. | 428/35.9 |
| 6,522,910 | B1 * | 2/2003 | Gregory | 600/427 |
| 6,865,494 | B2 * | 3/2005 | Duensing et al. | 702/38 |

* cited by examiner

*Primary Examiner*—Samir Ahmed
*Assistant Examiner*—Abolfazl Tabatabai
(74) *Attorney, Agent, or Firm*—Tillman Wright, PLLC; James D. Wright; Chad D. Tillman

(57) ABSTRACT

A system and method for non-destructive functional imaging and mapping of electrical excitation of biological tissues with the help of electromagnetic ("EM") field tomography and spectroscopy using a sensitive material (solution) added/injected into the biological tissue or in circulation system, characterized by having a dielectrical properties that is a function of electrical field, generated by biological tissue, plurality of EM field sources-detectors located around a biological object, so an object under a study is inside an EM field domain, and a control subsystems functionally coupled to the plurality of sources-detectors for selectively controlling function of the plurality of sources-detectors and for detected EM field from the plurality of sources-detectors so that multiple modality EM field is generated on a selected plurality of sources-detectors and detected by a selected plurality of sources-detectors after being interferenced by the object under a study and a signal inversion means operably connected to the control means for inversion of EM fields detected by a plurality of EM field detectors so an image of the object under a study and a spread of electrical excitation of biological tissue are reconstructed.

63 Claims, 17 Drawing Sheets

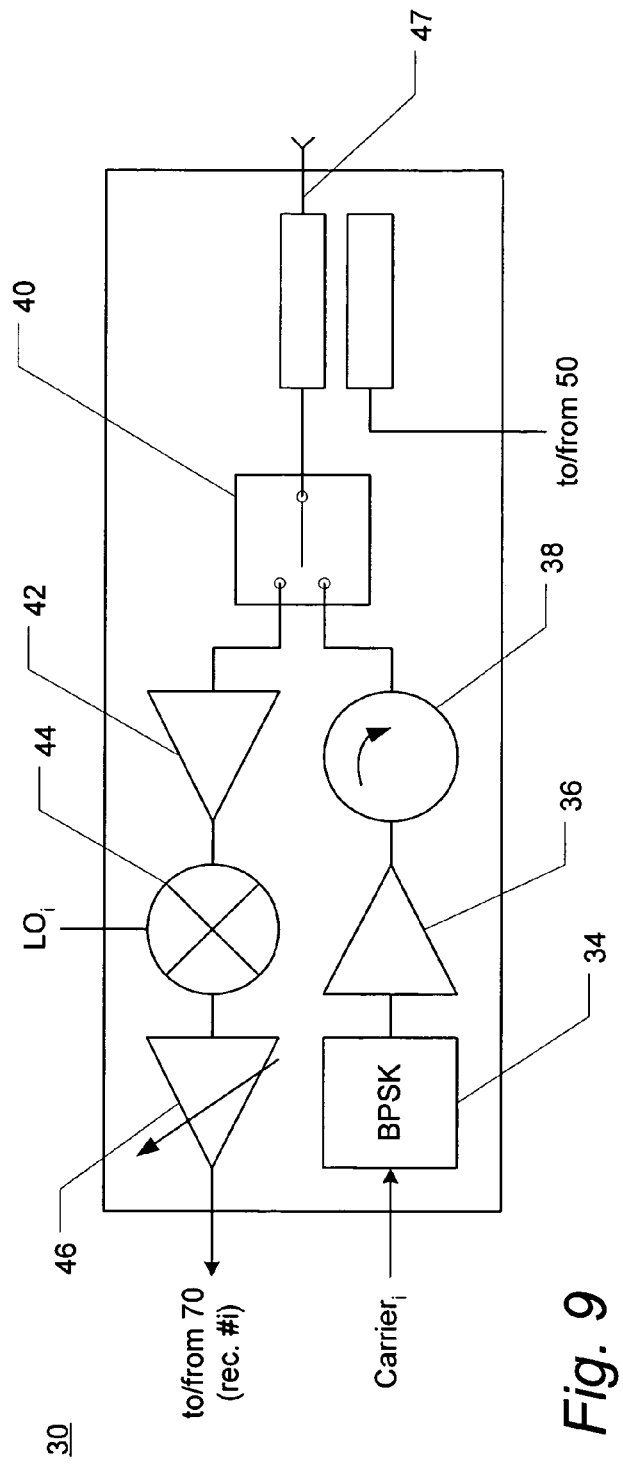
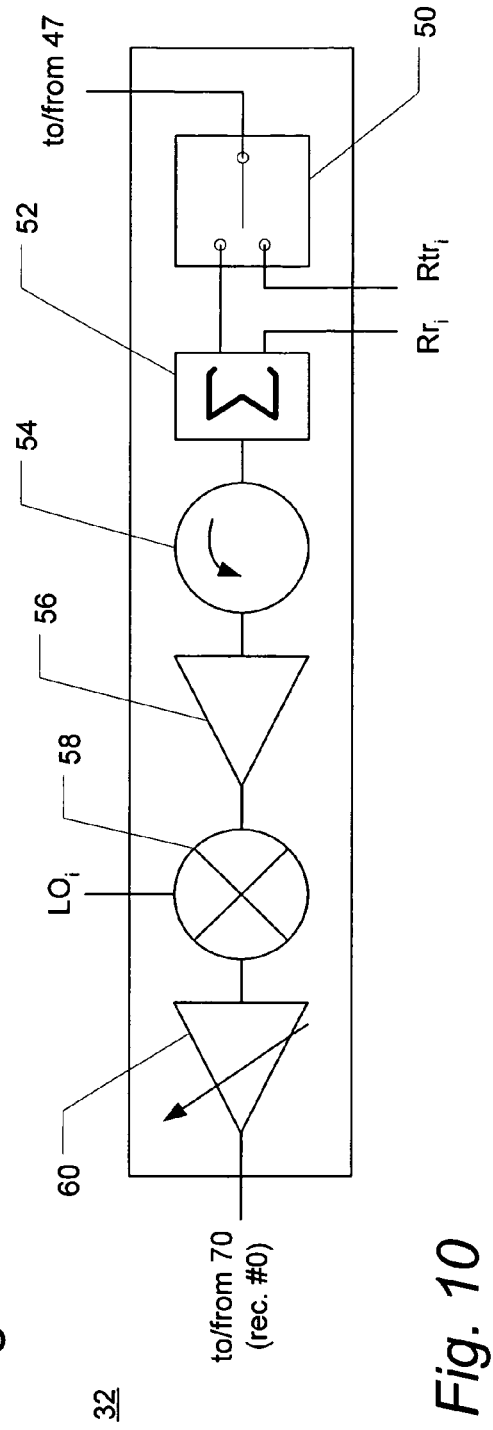
Fig. 9
Fig. 10

SYSTEM AND METHOD FOR NON-DESTRUCTIVE FUNCTIONAL IMAGING AND MAPPING OF ELECTRICAL EXCITATION OF BIOLOGICAL TISSUES USING ELECTROMAGNETIC FIELD TOMOGRAPHY AND SPECTROSCOPY

CROSS-REFERENCE TO RELATED APPLICATION

This application is entitled to the benefit of, and claims priority to, provisional U.S. Patent Application Ser. No. 60/429,272 filed Nov. 26, 2002 and entitled "SYSTEM AND METHOD FOR NON-DESTRUCTIVE FUNCTIONAL IMAGING AND MAPPING OF ELECTRICAL EXCITATION OF BIOLOGICAL TISSUES USING ELECTROMAGNETIC FIELD TOMOGRAPHY AND SPECTROSCOPY," the entirety of which is hereby incorporated by reference.

BACKGROUND OF THE PRESENT INVENTION

1. Field of the Present Invention

The present invention relates generally to electromagnetic field tomography and spectroscopy, and in particular, to the non-invasive functional imaging, detection and mapping of electrical excitation of a biological tissue with the help of electromagnetic field tomography and spectroscopy using a sensitive material (solution), injected into the biological tissue or in the circulation system, that is characterized by having dielectrical properties that are a function of the electrical field generated by biological excited tissue. The invention includes several versions of the systems differentiated on the basis of multiple frequency, polarization and type of sensitive material (solution) utilization. Further, the invention includes computer implemented software specifically configured and tailored for the system and method for non-invasive detection and mapping of electrical excitation of biological tissue with the graphical and three-dimensional tomographic imaging interface.

2. Background

It has long been known that within the electromagnetic spectrum, biological tissues have different electrical/dielectrical properties, and consequently, visual images of such tissues may be produced based on these properties. For example, it is known that the dielectrical properties of tissues with high (muscle) and low (fat and bone) water content are significantly different. During the last decade the changes in the dielectrical properties of tissues caused by various physiological and pathological alterations have been intensively studied. It has been demonstrated that dielectrical properties of malignant tumors and normal tissues are different in breast, lung, colon and liver. It has also been demonstrated that ischemia, infarction and hypoxia change the dielectrical properties of myocardial tissue. The amount of those differences (i.e., the contrast in their dielectrical properties) varies with frequency, type of tissue and the presence and type of disease, and the magnitude of variation may range from a few percentage points up to 4–5 times between the normal tissue and the diseased tissue. These examples demonstrate a high potential for the use of electromagnetic tomography in biomedical applications.

As a result, microwave tomography has been in the scope of interest of research groups for several years. For example, research by at least some of the present inventors has resulted in U.S. Pat. Nos. 5,715,819, 6,026,173 and 6,333,087 for microwave tomographic and spectroscopic systems and methods for detection of physiological and pathological conditions of biological tissues and physiological imaging of such tissues. The entirety of each of these patents is incorporated herein by reference.

Unfortunately, the research and development of this technology for biomedical applications has also met with significant difficulties. One such difficulty is the high attenuation of electromagnetic fields within the body. Attenuation is less at lower frequencies, but unfortunately, lower frequencies also result in lower spatial resolution. The compromise between attenuation and spatial resolution forms a frequency optimum for microwave imaging. J. C. Lin theoretically estimated that the frequency spectrum from 2 GHz to 8 GHz is the optimum for microwave imaging of biological tissue. Our estimations suggest that microwave imaging of whole scale biological objects with reasonable acquisition time and spatial resolution of 6–8 mm can be performed at frequencies near 1 GHz. Of course, experimentally achieved spatial resolution cannot compete with the spatial resolution achieved in X-ray imaging, simply because of the large difference in wavelength.

However, the possibility of imaging physiological and pathological conditions of tissues, highlighted earlier, makes this technology promising. For example, it has been determined that microwave tomography and spectroscopy are capable for detection of changes in myocardial blood supply, tissue hypoxia, myocardial ischemia and infarction, i.e. functional imaging. Research by at least some of the present inventors has experimentally proved that a tissue's dielectrical properties are a sensitive indicator of its functional and pathological conditions and the degree of such changes is large enough to be tomographically imaged.

FIG. 1 is a graphical representation of the changes of myocardial $\epsilon''$ following short time 20%, 40%, 60% and 100% blood flow reduction. The changes of myocardial $\epsilon''$ following short time 20%, 40%, 60% and 100% blood flow reduction. Summarized data for group of seven canines are presented as normalized on the baseline values. Data for three frequencies (0.2 GHz, 1.1 GHz, and 6.0 GHz) are expressed as mean +/− SD.

FIGS. 2A & 2B are graphical illustrations of the spectral changes in myocardial permittivity $\epsilon'$ and resistance $\rho$, respectively, during 10% hypoxia. The percent difference from the mean baseline data, summarized for the group of 7 canines, is shown. The bar graph inserted into the bottom right of FIG. 2A represents group averaged changes in arterial blood pH and $pO_2$.

FIGS. 3A and 3B are graphical illustrations of the spectral changes in myocardial permittivity $\epsilon'$ (A) and resistance $\rho$ (B) during 2 hours acute ischemia. The percent difference from the mean baseline data, summarized for a group of 6 canines is shown.

FIG. 4 is a graphical illustration of the changes in myocardial dielectric properties ($\epsilon@$) for 2-week-old canine myocardial infarction. Summarized data for a group of five canines are presented as mean percent change +/− SD in dielectrical values from normal zones of the infarcted hearts. The values are compared with fresh tissue from a 10-year-old human post-infarction aneurysm.

FIGS. 5A & 5B are reconstructed electromagnetic tomographic images of excised canine heart (longitudinally view through the long axis base to apex for $\epsilon'$-top and transversal view through an area with significant infarction injury for $\epsilon''$-bottom) together with anatomical slices. The frequency is 1 GHz, and the scales are in centimeters.

However, microwave tomography and spectroscopy do not appear to be capable of detecting changes in the dielectrical properties of myocardium, caused by a spread of electrical excitation in tissue. Preliminary studies, conducted in tissue bath using cardiac excited tissue and electromechanical uncoupling pharmaceutical agents, have indicated that the dielectrical properties of cardiac excited tissue change during the excitation cycle. The exact degree of such changes is unknown at present time, but it appears to be less than 1 percent. This is a relatively small variation in tissue dielectrical properties to be reliably reconstructed using modern electromagnetic tomographic technologies. Further, it is difficult to acquire the necessary data during the short period of time available during the circulation cycle.

Thus, previous approaches to localizing the origin of such phenomenon as cardiac arrhythmias have depended on one of three principal techniques: catheter mapping, electrical excitation mapping during cardiac surgery, or body surface mapping of electrical potentials and magnetic fields. Each of these techniques has limitations. For example, catheter mapping and excitation mapping during surgery are inherently invasive, provide only limited access, and are time sensitive. On the other hand, body surface mapping can be performed in a non-invasive, low-risk manner, but with such poor definition that the data is generally considered unsuitable for directing subsequent therapy. Thus, a need exists for a non-invasive system by which electrical excitation of a biological tissue may be reliably detected and mapped.

Another difficulty faced in the use of microwave tomography for the purposes described hereinabove is the wave character of the distribution of the electromagnetic field within and around a body. These lead to a highly complicated image reconstruction theory, i.e. the problem of diffraction tomography. The linear, ray approach applicable to X-ray tomography does not work properly with regard to microwave tomography. Thus, a need exists for advanced, non-linear diffraction approaches to the process of image reconstruction.

SUMMARY OF THE PRESENT INVENTION

The present invention comprises a system and method for non-destructive functional imaging and mapping of electrical excitation of biological tissues with the help of electromagnetic ("EM") field tomography and spectroscopy using a sensitive material or solution introduced into the biological tissue or the circulation system, characterized by having dielectrical properties that are a function of electrical field generated by the biological tissue, plurality of EM field sources-detectors located around a biological object, so an object under a study is inside an EM field domain, and a control subsystems functionally coupled to the plurality of sources-detectors for selectively controlling function of the plurality of sources-detectors and for detected EM field from the plurality of sources-detectors so that multiple modality EM field is generated on a selected plurality of sources-detectors and detected by a selected plurality of sources-detectors after interacting with the biological object and a signal inversion means operably connected to the control means for inversion of EM fields detected by a plurality of EM field detectors so an image of the biological object and the spread of electrical excitation of the biological object are reconstructed.

The utility of this invention encompasses many fields of medicine. In particular, the embodiments of the present invention relate to non-destructive functional imaging and mapping of electrical excitation of biologically excited tissues, including but not limited to cardiac tissues, nervous tissue and musculoskeletal tissue. This allows for rapid and accurate assessment of functional and pathological conditions of biological tissues and localization of sources of irregularities (arrhythmogeneties) in the process of an electrical excitation of biological tissues. The identification of the source of such irregularities (arrhythmogeneties) has enormous practical utility in selecting a proper treatment and therapy strategy.

Further areas of applicability of the present invention will become apparent from the detailed description provided hereinafter. It should be understood that the detailed description and specific examples, while indicating the preferred embodiment of the invention, are intended for purposes of illustration only and are not intended to limit the scope of the invention.

BRIEF DESCRIPTION OF THE DRAWINGS

Further features, embodiments, and advantages of the present invention will become apparent from the following detailed description with reference to the drawings, wherein:

FIG. 9 is a block diagram of one of the source-detector modules of FIG. 8;

FIG. 10 is a block diagram of the R-channel module of FIG. 8;

DETAILED DESCRIPTION OF THE PREFERRED EMBODIMENTS

Figure 1:
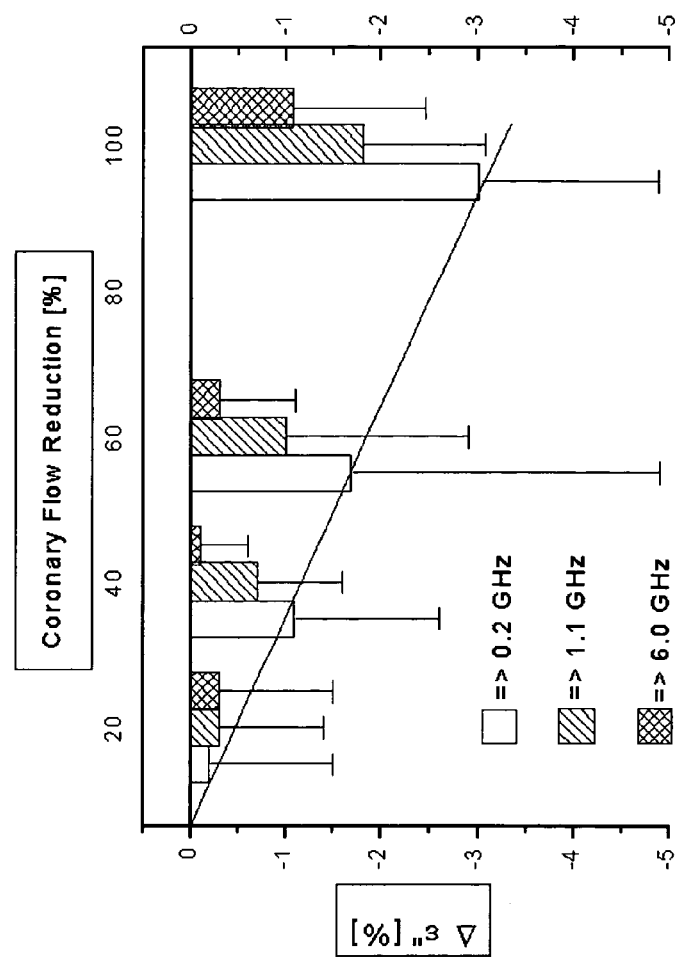
FIG. 1 is a graphical representation of the changes of myocardial $\epsilon''$ following short time 20%, 40%, 60% and 100% blood flow reduction.

Referring now to the drawings, in which like numerals represent like components throughout the several views, the preferred embodiments of the present invention are next described. The following description of the preferred embodiment(s) is merely exemplary in nature and is in no way intended to limit the invention, its application, or uses.

Figure 6:
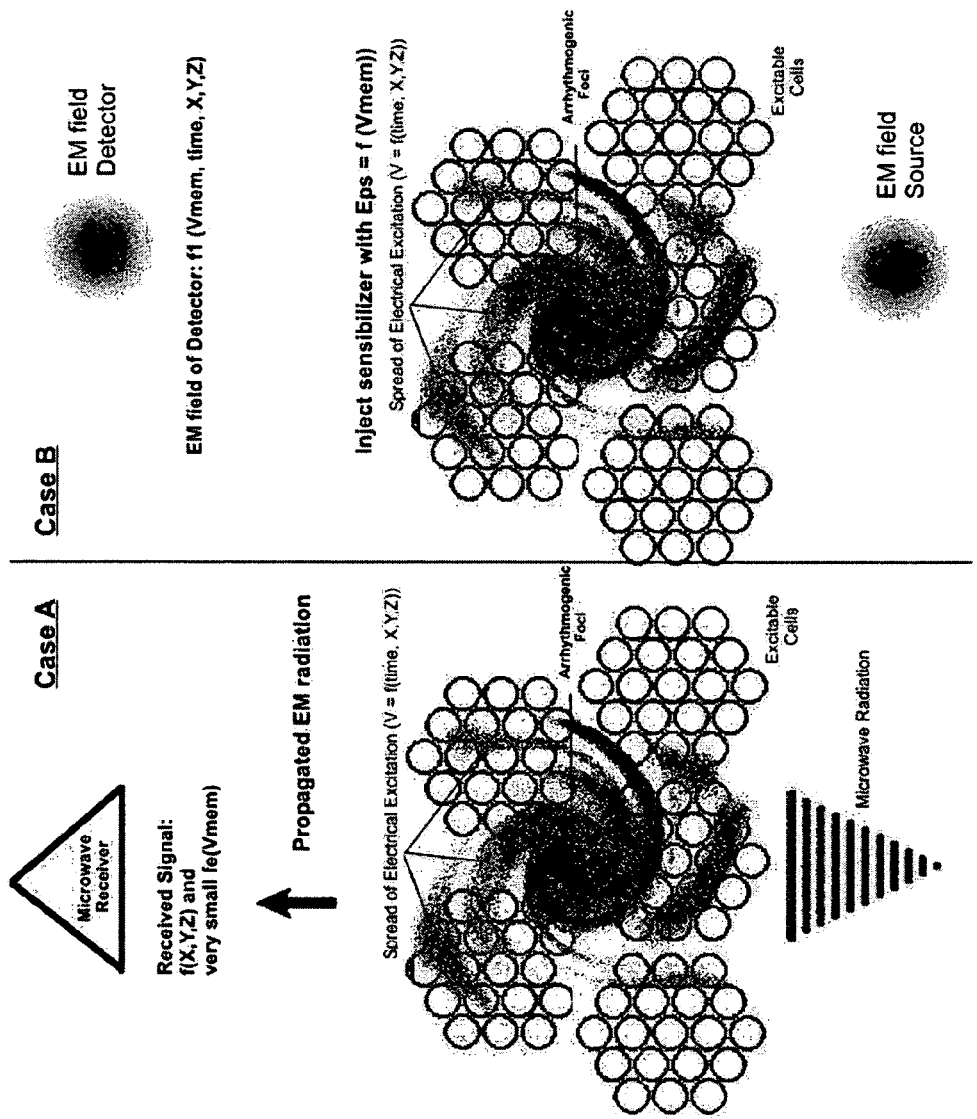
FIG. 6 is a schematic view of a method for non-destructive functional imaging and mapping of electrical excitation of biological excited tissues using electromagnetic tomography and an injection of a sensitive (contrast) material (solution) into the biological tissue or in circulation system, characterized by having a dielectrical properties that is a function of electrical field, generated by biological excited tissue (Case B) compared with traditional method of microwave tomographic imaging (Case A)

The major idea of the present invention is to use a sensitive material (solution) injected into a biological tissue 19 or in the circulation system in order to detect and map an electrical excitation of the biological tissue 19. FIG. 6 is a graphical illustration of a method for non-destructive functional imaging and mapping of electrical excitation of biological excited tissues 19 using electromagnetic tomography and an injection of a sensitive (contrast) material (solution) into the biological tissue 19 or in circulation system, characterized by having a dielectrical properties that is a function of electrical field, generated by biological excited tissue 19 (Case B) compared with traditional method of microwave tomographic imaging (Case A). The dielectrical properties of this material (solution) are a function of electrical field, generated by biological excited tissue 19 itself, so they can be reconstructed with the help of microwave (electromagnetic) tomography, and consequentially the spread of electrical excitation of biological tissue 19 can be non-invasively reconstructed.

Figure 7:
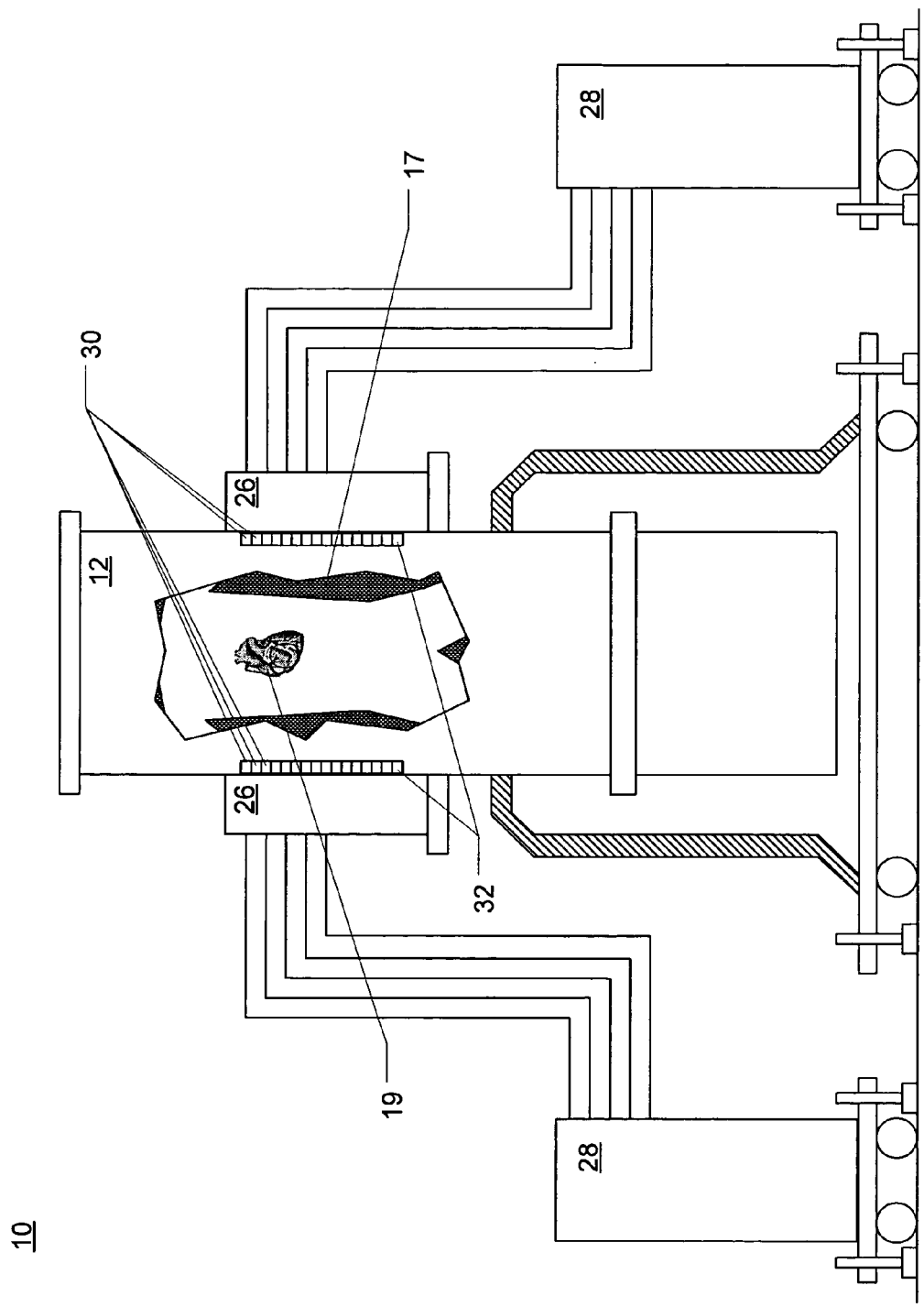
FIG. 7 is a schematic view of an EM field tomographic spectroscopic system for non-destructive functional imaging and mapping of electrical excitation of biological tissues using a sensitive (contrast) material (solution) injected into the biological tissue or in circulation system, characterized by having a dielectrical properties that is a function of electrical field, generated by biological excited tissue, in accordance with the preferred embodiments of the present invention.

FIG. 7 is a schematic view of an EM field tomographic spectroscopic system 10 for non-destructive functional imaging and mapping of electrical excitation of biological tissues 19 using a sensitive (contrast) material (solution) injected into the biological tissue 19 or in circulation system, characterized by having a dielectrical properties that is a function of electrical field, generated by biological excited tissue 19, in accordance with the preferred embodiments of the present invention. As illustrated in FIG. 7, the system 10 includes a working chamber 12, a plurality of "EM field source-detector" clusters 26, an equal number of intermediate frequency ("IF") detector clusters 28, and a control system (not shown in FIG. 7, but illustrated in block diagram form in FIG. 11). Although only two EM field source-detector clusters 26 and two IF detector clusters 28 are shown, it should be clear that a much larger number of each, sometimes denoted herein by N, may (and preferably should) be used.

The working chamber 12 may be a watertight vessel of sufficient size to accommodate a human body, and may have different shapes and sizes, the selection of which would be readily apparent to one of ordinary skill in the art. The working chamber 12 and its EM field clusters 26, as well as the IF detector clusters 28, may be mounted on carts in order to permit the respective components to be moved if necessary, and the carts may then be locked in place to provide stability.

Figure 8:
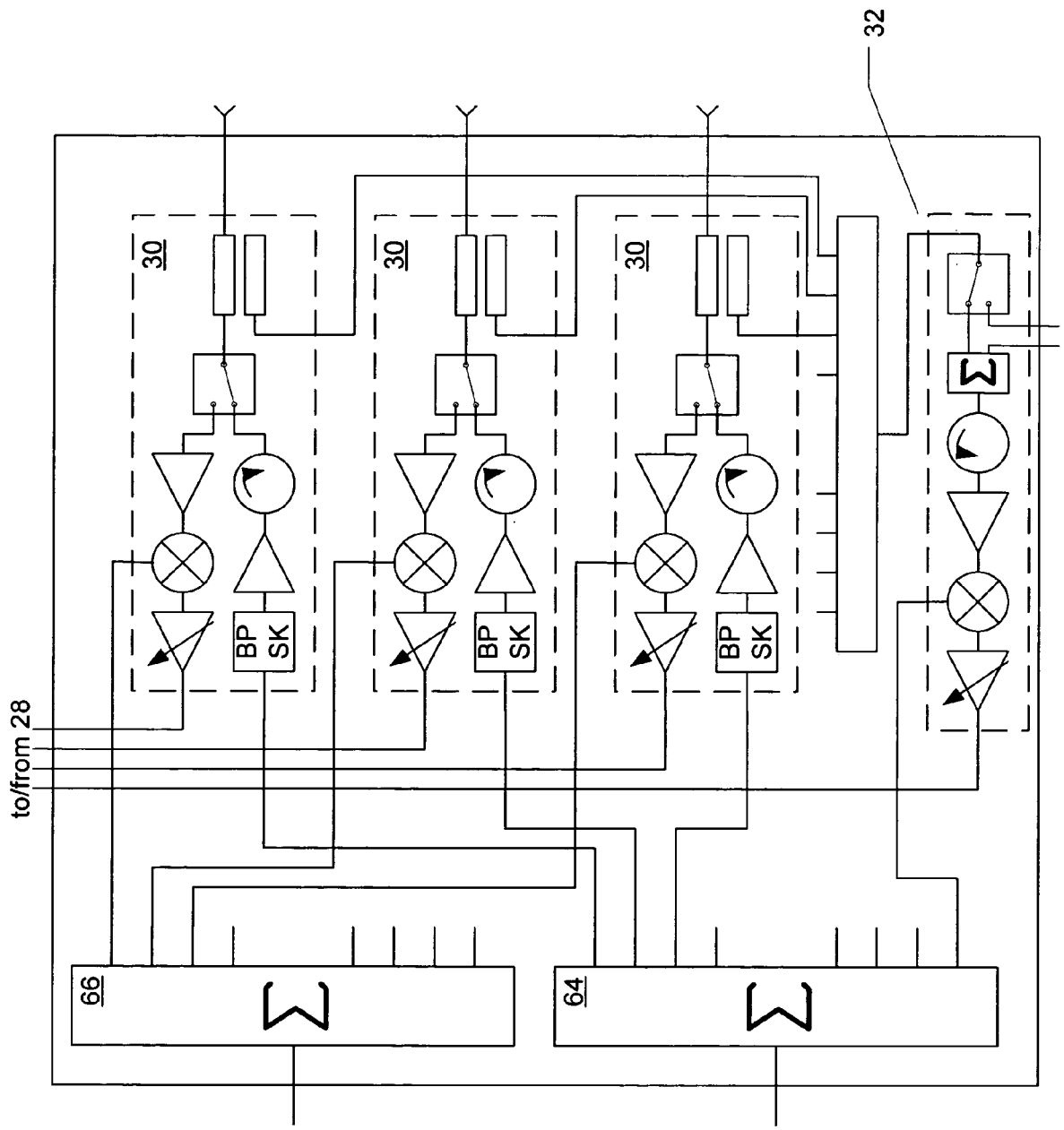
FIG. 8 is a block diagram of one of the EM field source-detector clusters of FIG. 7, wherein the cluster is in its source state.

FIG. 8 is a block diagram of one of the N EM field clusters 26 of FIG. 7, wherein the cluster 26 is in its source state. Each EM field cluster 26 is a main operation unit that may function as an electromagnetic field generator (i.e., an electromagnetic source) or as an electromagnetic field detector. Each cluster 26 has a plurality of source-detector modules 30, one reference channel ("R-channel") module 32 and a pair of distribution blocks 64, 66, as well as at least two precision attenuators. The number of source-detector modules 30 (three being shown here) in each EM field cluster 26 may sometimes be denoted herein by M. In general, the more source-detector modules 30 that are used, the greater the precision of the system 10. However, because of the large amounts of data that are created, it may be preferable to use between 500 and 1500 source-detector modules 30, with an optimum number near 1000, organized into N EM field clusters 26, with the value of N selected based generally on manufacturability and convenience.

FIG. 9 is a block diagram of one of the M source-detector modules 30 of FIG. 8. Each source-detector 30 includes a BPSK modulator 34, a power amplifier 36, a direct uncoupler 38, a switch 40, a low noise amplifier ("LNA") 42, a mixer 44, a programmable gain amplifier ("PGA") 46 and an antenna 48. The switch 40 functions to connect the antenna 48 into the system 10 as an EM source or as an EM detector. When connected as a source (i.e., when the switch 40 is in the lower of the two positions shown in FIG. 9), an input signal provided by one of the distribution blocks 64 (as shown in FIG. 8) is modulated by the BPSK modulator 34, amplified by the amplifier 36 and uncoupled by the direct uncoupler 38 before passing through the switch 40 to the antenna 48. On the other hand, when connected as a detector (i.e., when the switch 40 is in the upper of the two positions shown in FIG. 9), the signals received by the antenna 48 pass through the switch 40 to the LNA 42 where they are amplified and then mixed with a reference signal provided by the second distribution block 66 (as shown in FIG. 8) and then amplified again by the PGA 46.

FIG. 10 is a block diagram of the R-channel module 32 of FIG. 8. As described previously, there are preferably a plurality (M) of source-detector modules 30 in each EM field cluster 26 but only a single R-channel module 32. The R-channel module 32 includes a switch 50, an adder 52, a direct uncoupler 54, an LNA 56, a mixer 58 and a PGA 60. The switch 50 controls whether the R-channel module 32 is in its source state or its detector state. When the R-channel module 32 is in its source state (i.e., when the switch 40 is in the upper of the two positions shown in FIG. 10), output signals from the source-detector modules 30 are passed through the adder 52 and the direct uncoupler 54 and are amplified by the LNA 56 before being mixed with a reference signal and amplified again by the PGA 60. On the other hand, when the R-channel module 32 is in its detector state (i.e., when the switch 40 is in the lower of the two positions shown in FIG. 10), a reference signal is passed straight through to the source-detector modules 30 where it is coupled with the signals received by the respective antennae 48.

Figure 11:
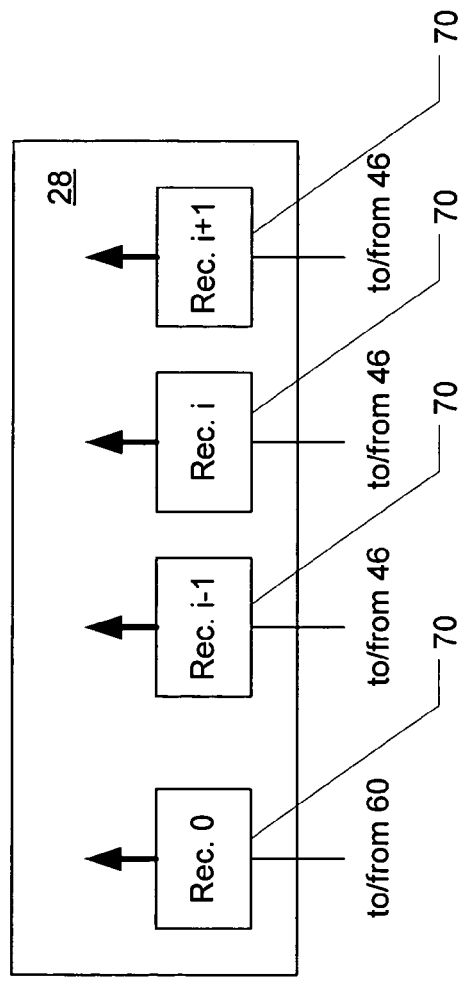
FIG. 11 is a block diagram of one of the IF detector clusters of FIG. 7.

FIG. 11 is a block diagram of one of the N IF detector clusters 28 of FIG. 7. Each IF detector cluster 28 includes a family of M+1 digital correlation detectors 70 for M test signals (one from each of the source-detector modules 30 in a corresponding EM field cluster 26) and one reference channel signal. These digital detectors 70 allow for the informative/working bandwidth of the signal to be selectively passed while restricting other artifacts. Each IF detector cluster 28 also includes a cluster manager, a bus, and a power supply.

Figure 12:
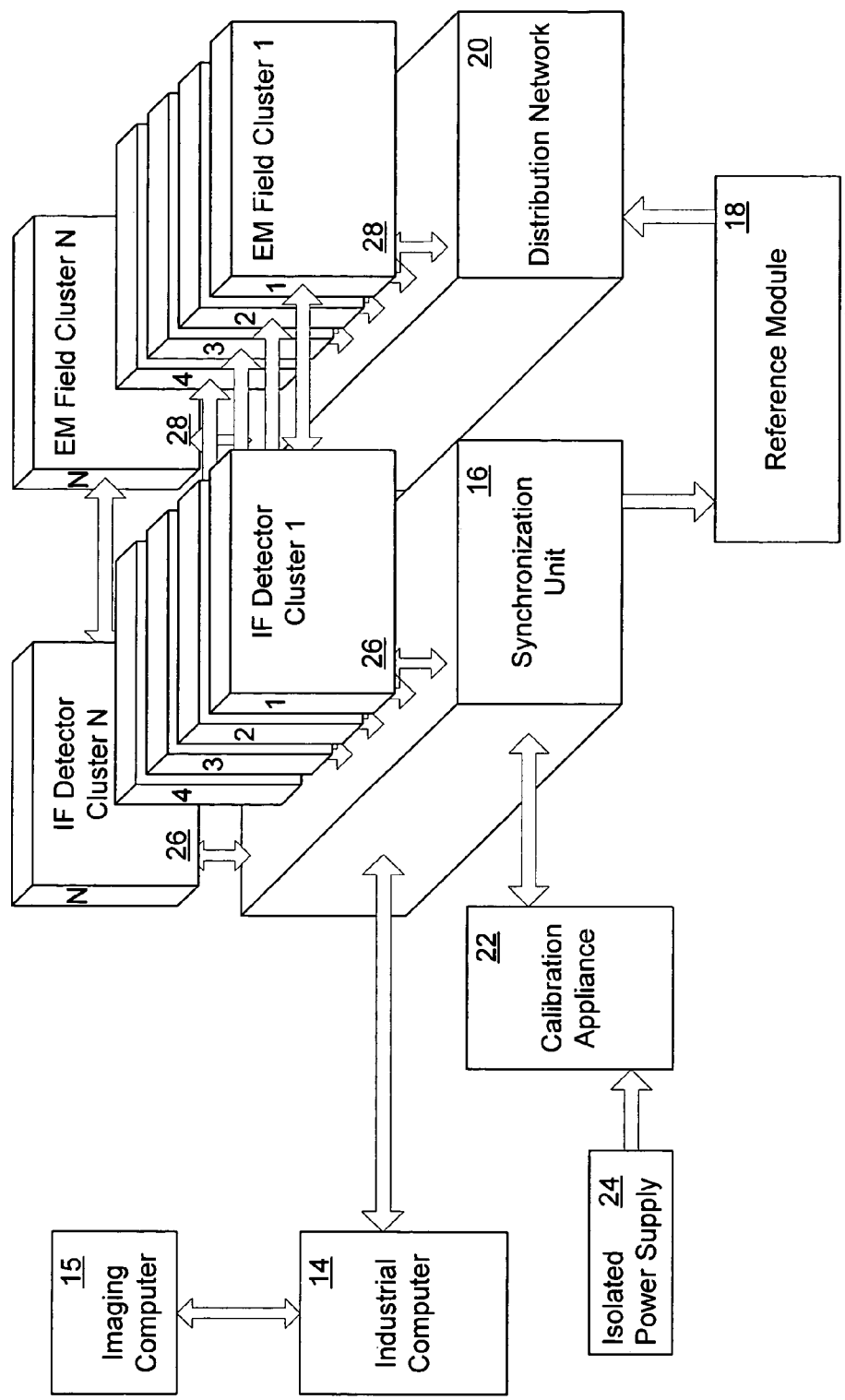
FIG. 12 is a block diagram of the control system for the EM field clusters and IF detector clusters of FIG. 7.

FIG. 12 is a block diagram of the control system for the EM field clusters 26 and IF detector clusters 28 of FIG. 7. The control system includes a control computer 14, an imaging computer 15, a synchronization unit 16, a reference module 18, a distribution network 20, a calibration appliance 22 and a power supply 24. The control computer 14 controls the overall system function, data acquisition, system tuning and calibration and transforms all raw data to the imaging computer 15 for further data inversion and imaging. The control computer 14 may be a conventional personal computer, such as an Intel-based advanced-version PC, with an RS-488.2 port and appropriate software to control the system 10. The synchronization unit 16 is a module that includes a system manager and a system hub. Together, they provide data exchange with the control computer 14 (preferably via a USB 2.0 or Firewire link) and the control managers of the various clusters 26, 28, and also provide synchronization of system operations.

The reference module 18 includes two generators, one or more thermostats for temperature stabilization of the function of the reference channels, a BPSK modulator for phase-modulation, power dividers, attenuators and the like. The two generators are precision generators that generate stable CW signals: $Carrier_{ref}$ and $LO_{ref}$. These generators are controlled and tuned by the control computer 14 through an interface. The distribution network 20 is a commutation unit for receiving the carrier and local oscillator reference signals ($Carrier_{ref}$ and $LO_{ref}$) and the Rr and Rtr reference signals ($Rr_{ref}$ and $Rtr_{ref}$) from the reference module 18 and distributing them to each of the EM field clusters 28.

The calibration appliance 22 is used for calibration and fine-tuning of the system 10. The calibration appliance 22 includes a calibration source, one or more (preferably two) calibration antennae, precision drives and one or more (preferably three) calibrated phantoms. Calibration antennae and phantoms may be precisely positioned at any point inside the working chamber with the help of precision positioning drivers. The isolated power supply 24 provides stable power for the system. One power supply suitable for use with the present invention is a 190/380 3-phase, 10 kVA AC network power supply. Of course, the exact requirements for the power supply 24 may depend upon the power system specifications of the country in which the system 10 is to be operated.

Figure 2A:
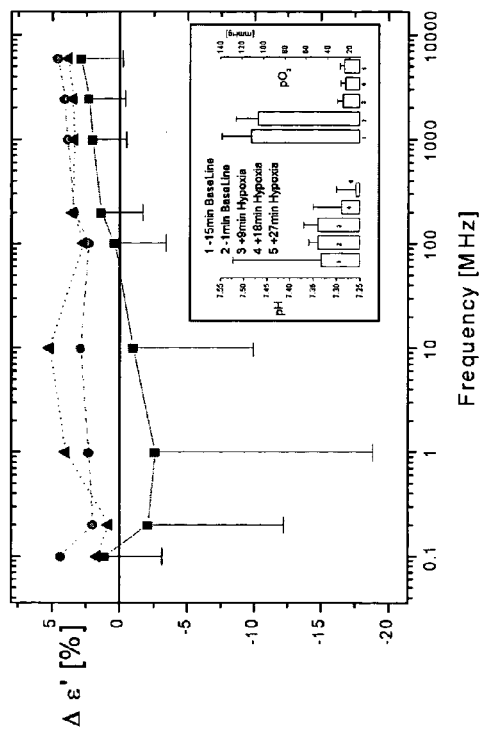
FIGS. 2A & 2B are graphical illustrations of the spectral changes in myocardial permittivity $\epsilon'$ and resistance $\rho$, respectively, during 10% hypoxia.
Figure 2B:
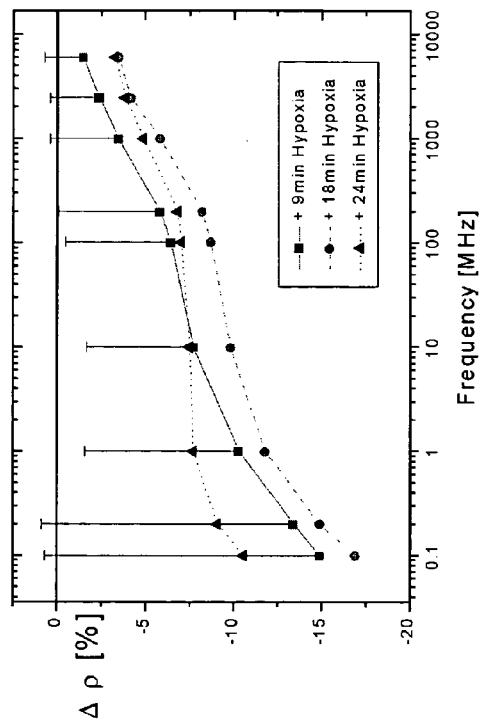
Figure 3B:
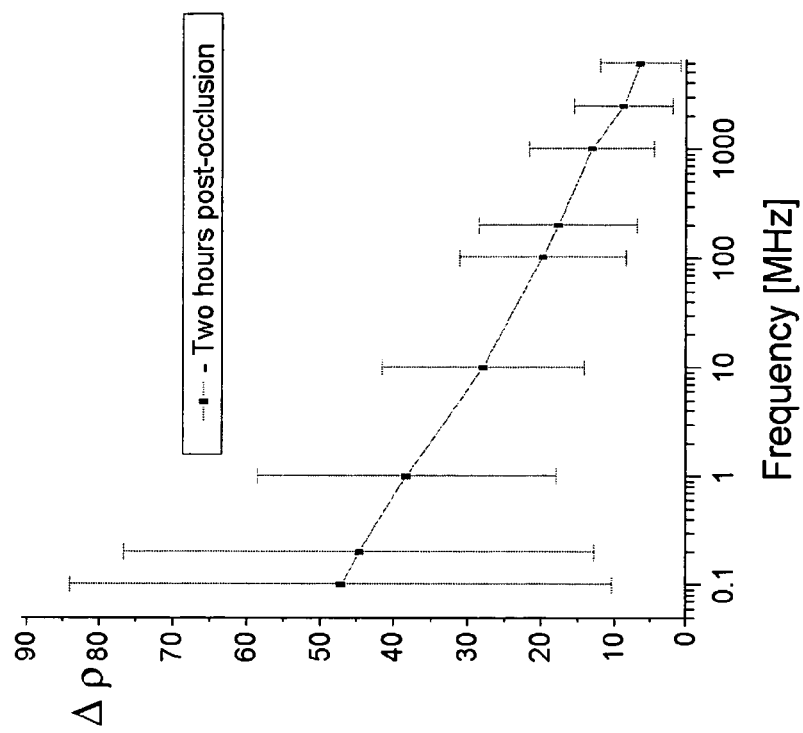
FIGS. 3A & 3B are graphical illustrations of the spectral changes in myocardial permittivity $\epsilon'$ and resistance $\rho$, respectively, during 2 hours acute ischemia.
Figure 3A:
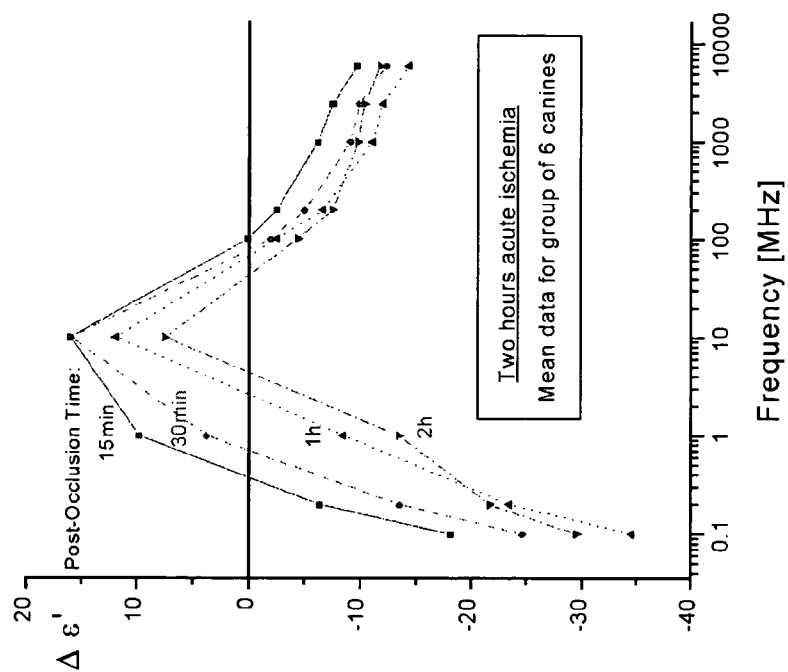
Figure 4:
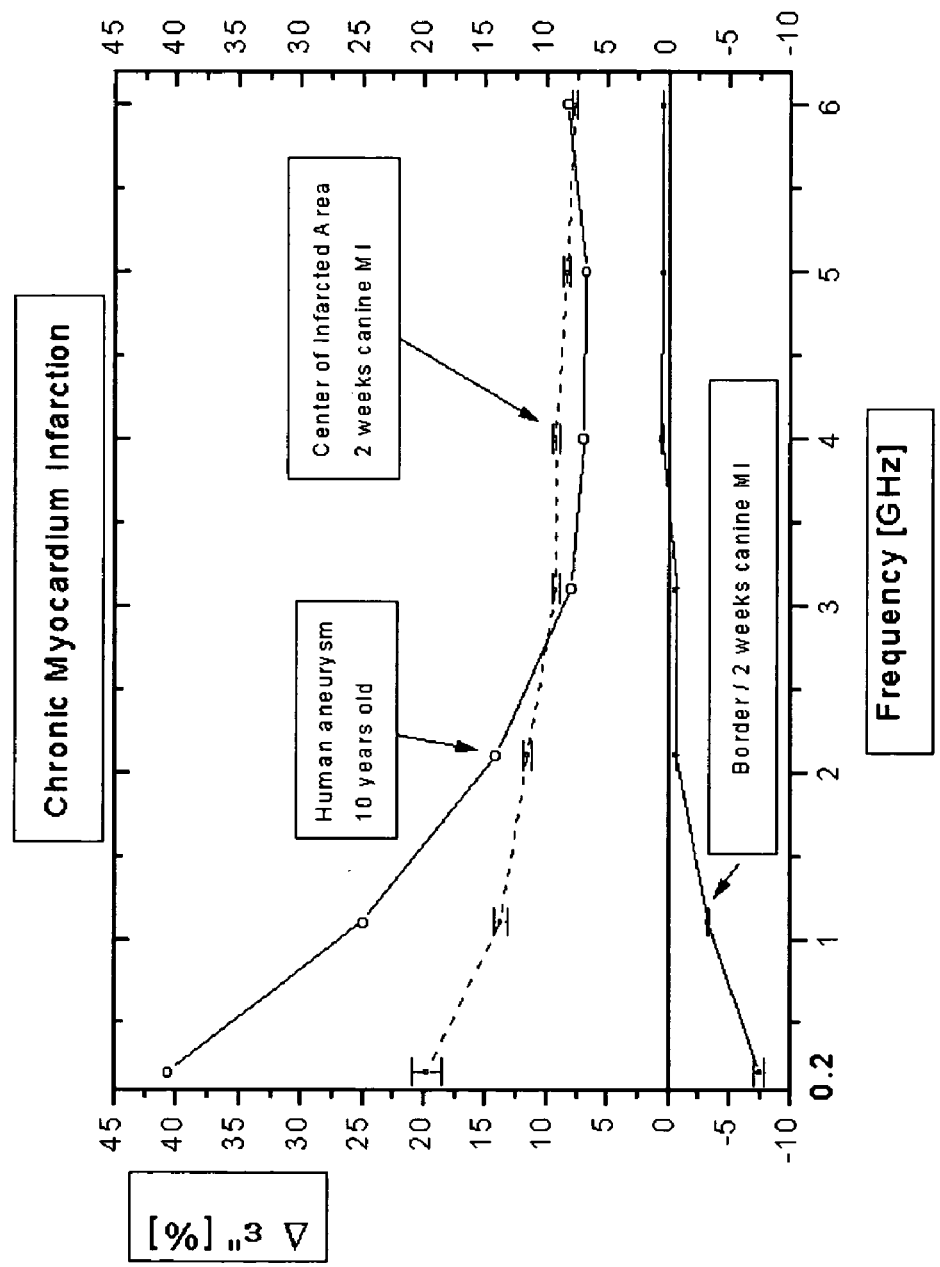
FIG. 4 is a graphical illustration of the changes in myocardial dielectric properties ($\epsilon@$) for 2 week old canine myocardial infarction.
Figure 5A:
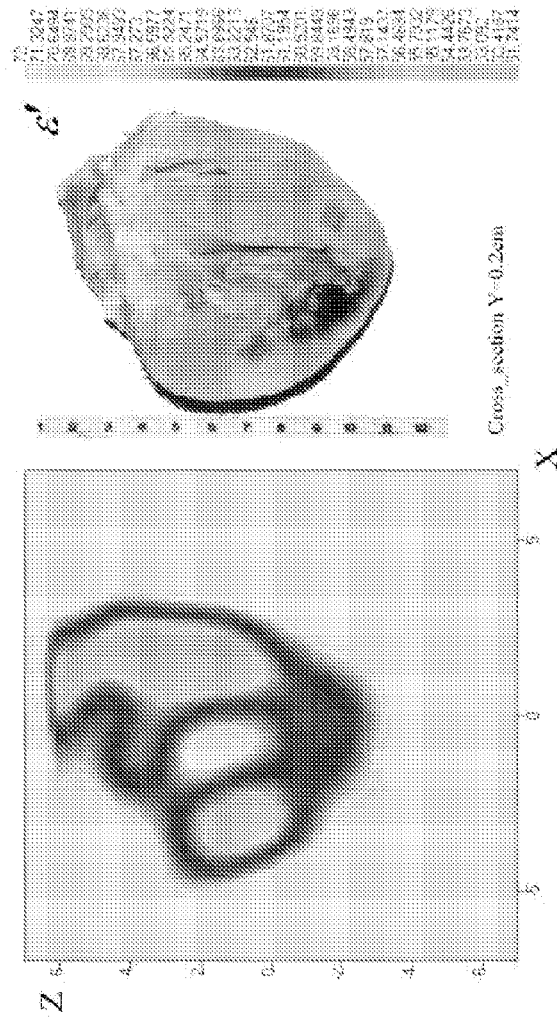
FIGS. 5A & 5B are reconstructed electromagnetic longitudinal tomographic images of an excised canine heart together with anatomical slices.
Figure 5B:
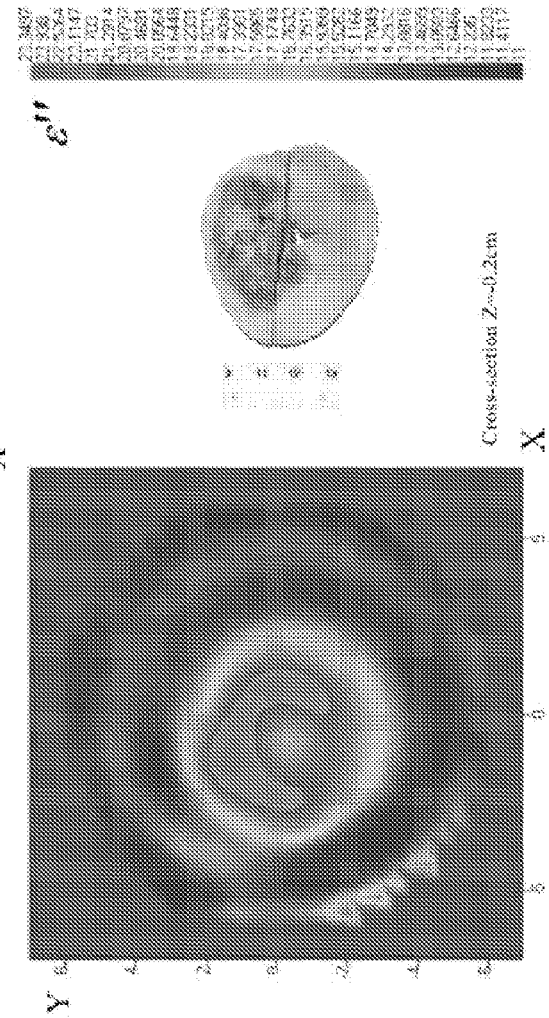
Figure 13:
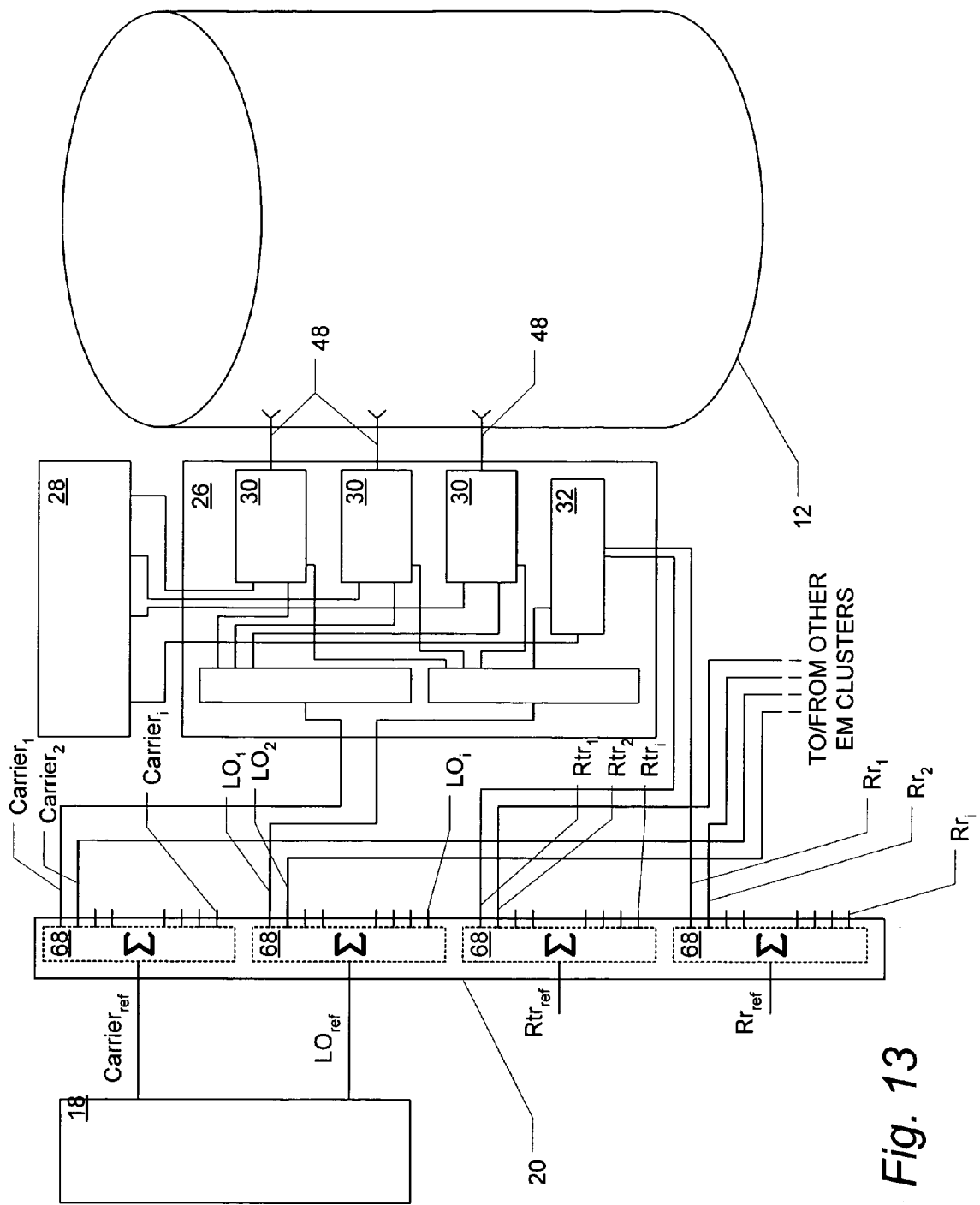
FIG. 13 is a block diagram illustrating the integration of the control system of FIG. 11 with the system of FIG. 7.

FIG. 13 is a block diagram illustrating the integration of the control system of FIG. 11 with the system 10 of FIG. 7. Each EM field cluster 26 is disposed adjacent the working chamber 12 such that its antennae 48 are located on or near the surface of the chamber 12. The outputs of the source-detector modules 30 and the R-channel module 32 of each EM field cluster 26 are connected to a corresponding IF detector cluster 28, and each IF detector cluster 28 is connected to both the corresponding EM field cluster 26 and the synchronization unit 16. The inputs of each EM field cluster 26 are connected to the distribution network 20. The distribution network 20 includes at least four distribution blocks 68, which may be 34-channel power dividers, and a system bus for distributing the various reference signals ($Carrier_{ref}$, $LO_{ref}$, $Rr_{ref}$ and $Rtr_{ref}$) to the EM field clusters 26. As illustrated in FIG. 12, one set of the four signals is provided to each EM field cluster 26. These signals are denoted $Carrier_i$, $LO_i$, $Rr_i$ and $Rtr_i$, where the first EM field cluster 26 (i.e., the one shown in FIG. 2F) receives $Carrier_1$, $LO_1$, $Rr_1$ and $Rtr_1$, the second EM field cluster 26 (not shown) receives $Carrier_2$, $LO_2$, $Rtr_2$ and $Rtr_2$, and so forth. Finally, as described previously, $Carrier_{ref}$ and $LO_{ref}$ are provided to the distribution network 20 by the reference module 18.

In use, the working chamber 12 is filled with one of a variety of solutions or gels 17 selected to match and provide biological compatibility with a biological tissue object 19 to be studied. Suitable solutions 17 may include, but are not limited to, water, salt solutions, sugar solutions, fatty emulsions and the like; these solutions may also be used as gel components. The object 19 to be studied may be injected with a sensitive material (solution) (or distributed in the object 19 via the circulation system) whose dielectrical properties are a function of the electrical field generated by the biological excited tissue 19 itself, so that they can be reconstructed via microwave (electromagnetic) tomography. Preferably, the injection materials or solutions are a multi-component media that includes ferroelectrics, such as barium modified strontium titanium oxide, of different grain sizes ranging from 0.5–100 µm. The grains preferably also include different shapes, including spheres, ellipsoids and cylinders. The materials may also include selected potentiometric dyes, such as merocyanine, rhodamine, cyanine, oxonol and naphthyl styryl, and/or selected potentiometric liquid crystals, such as MBBA, 7CB.

After injection, the object 19 is then positioned inside the working chamber 12 and the system 10 is activated. During operation of the system 10, each $Carrier_i$ signal from the signal generator in the reference module 18 is provided to a source-detector module 30, operating in its source mode as shown in FIGS. 8 and 9, where it is modulated using phase-shift modulation (in case of phase characterization) by pseudo-random code in order to distinguish each transmitting antenna 48 or source from the other antennae/sources 48, which are transmitting simultaneously. As described previously, the resultant signal is next amplified before passing through the direct uncoupler 38 to the appropriate source antenna 48. As a result, an incident EM field ("$E_{inc}$"), corresponding to the respective antenna 48 or channel, is formed in the vicinity of the object 19 under study. In addition, part of the signal creating the $E_{inc}$ field is uncoupled and passes to a receiver in the R-channel module 32 (one for each EM field cluster 26). In the R-channel module 32 this signal is mixed with a reference signal $Rr_i$. By subsequently comparing the resultant output with a known signal, $E_{inc}$ may thus be determined precisely as described below.

Figure 14:
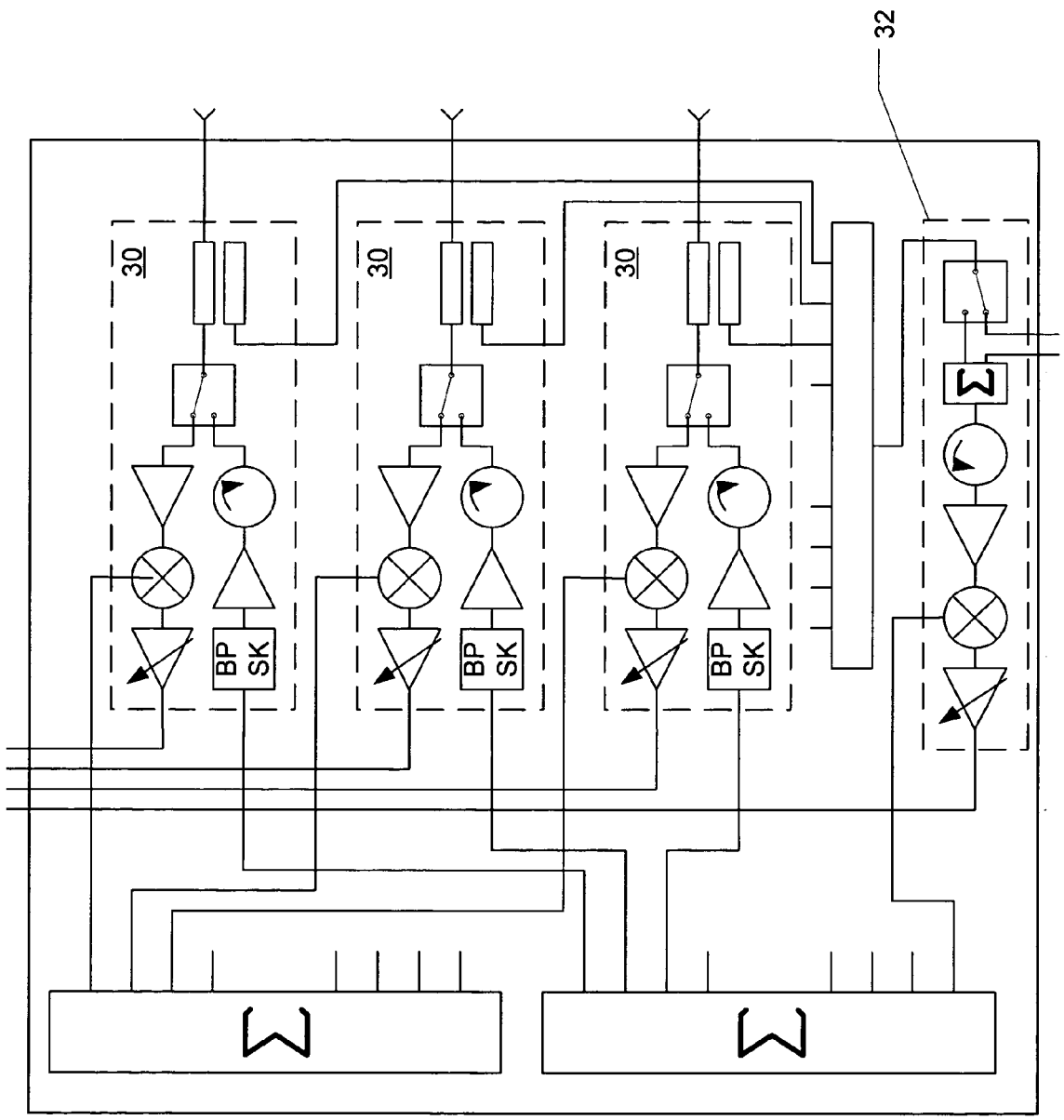
FIG. 14 is a block diagram of the EM field source-detector cluster of FIG. 8, wherein the cluster is in its detector state.

After interacting with the object 19 of interest, each "interferenced" or scattered EM field ($E_{sct}$) is detected by a corresponding detecting antenna 48 operating in its detector mode. FIG. 14 is a block diagram of the EM field source-detector cluster 26 of FIG. 8, wherein the cluster is in its detector state. The same reference signal $Rr_i$ described in the preceding paragraph is injected into the source-detectors 30 of the EM field cluster 26 (operating in detector mode) immediately downstream from the detecting (receiving) antenna 48. This allows for the R-channel signal $Rr_i$, which is known precisely, to pass through all parts of the detector 30 through which the $E_{sct}$ signal is passed. Therefore, an injection of the R-channel signal into the measuring portions of the source-detectors 30 in both source and detection mode allows for a significant decrease in artifacts caused by temperature and temporary instability of the channel electronics.

Figure 15A:
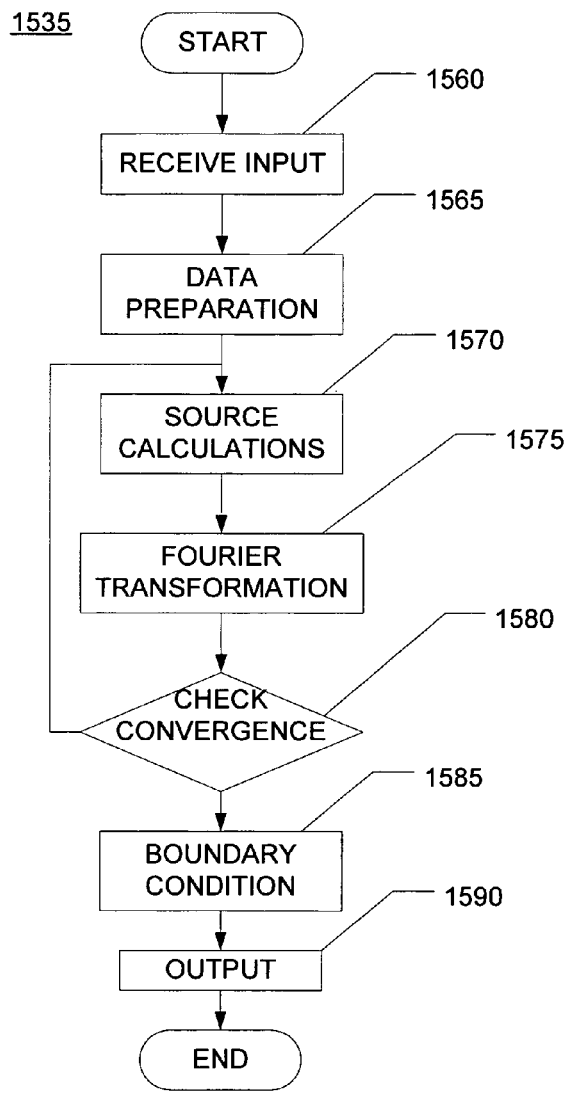
FIG. 15A is a flow diagram of the direct problem solver portion of the images reconstruction process.
Figure 15B:
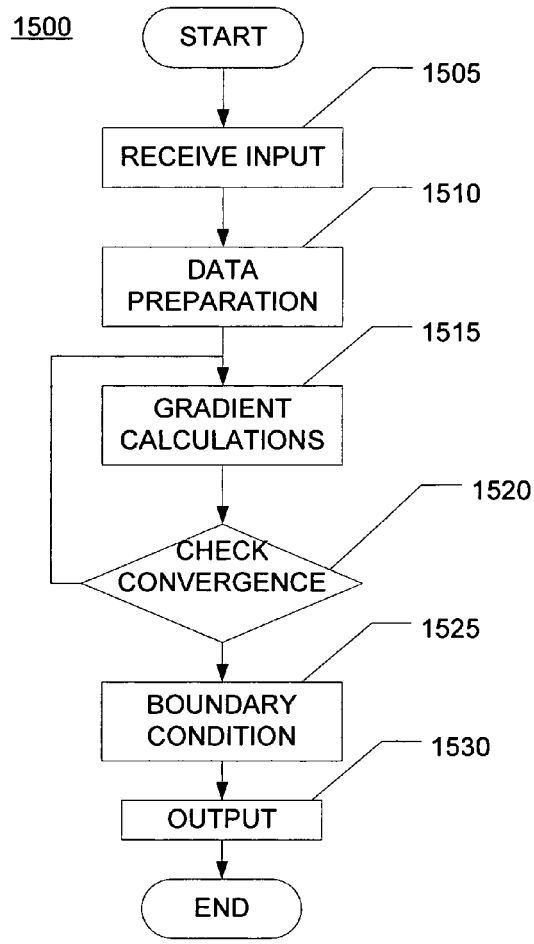
FIG. 15B is a flow diagram of the inverse problem solver portion of the images reconstruction process.
Figure 15C:
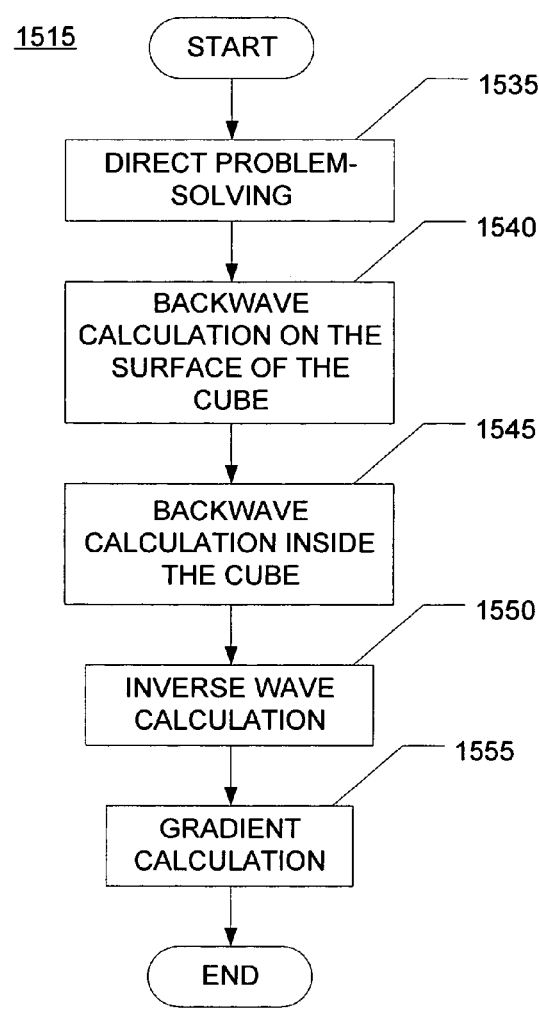
FIG. 15C is a flow diagram of the gradient calculation portion of the images reconstruction process.

The data and other information gathered by the system 10 is provided to the imaging computer 15. A novel process is carried out by the imaging computer 15 to solve an inverse problem of electromagnetic field tomography. It is based on the solution of a non-simplified three-dimensional ("3D") vector using Maxwell's equations. FIGS. 15A, 15B and 15C are flowcharts of this process. The method uses an iterative procedure based on gradient calculation approach with the following features, among others:

The method is based on minimization of the difference between model scattered fields and measured scattered fields.

The method uses the Tichonov's type of regularization.

One type of the calculation mesh is used in the method.

One step of the iterative procedure is performed as solving of the two sets of direct problems of the same dimension: modeling of the so-called direct wave and modeling of the inverse wave.

Both the direct wave and the inverse wave are calculated using nonreflecting boundary conditions.

Both the direct wave and the inverse wave are calculated on the same rectangular mesh.

In order to solve the direct problem a conjugate gradient method ("CGM") is used.

One step of the CGM uses the sine Fourier transform.

The wave equation for non-uniform media is used to solve the direct problem.

From a mathematical point of view, the methodology utilized in EM field tomography is an inverse problem. It may be formulated in terms of complex dielectrical properties $\epsilon$ and electrical and magnetic fields –E, H. The basis is a set of the Maxwell's equations:

$$cirlH = \frac{4\pi}{c}j + \frac{i\varepsilon\omega}{c}E \quad (1)$$

$$cirlE = -\frac{i\omega}{c}H$$

$$div(\varepsilon E) = 0$$

$$divH = 0$$

where E, H represent electrical and magnetic fields, respectively, and all other notations are standard.

It is more practical to rewrite these equations in a form of non-uniform wave equations:

$$\nabla^2 E + k^2 E - divgradE = 0 \quad (2)$$

where $$k^2 = \left(\frac{2\pi}{\lambda}\right)^2 \varepsilon,$$

and $\lambda$ is a wavelength in vacuum. The EM field tomographic system could be schematically represented as a chamber with the set of antennae on the surface of the chamber. As described previously, some antennae function as EM field sources while the others function as EM field detectors. It is useful to divide electric field E into incident $E_0$ field and scattered field $E_s$:

$$E_j = E_{oj} + E_{sj} \quad (3)$$

where j is the number of a particular transmitter or source. The equation (2) can be rewritten in the form:

$$\nabla^2 E_{sj} + k^2 E_{sj} - graddivE_{sj} = (k_0^2 - k^2)E_{0j} \quad (4)$$

where $k_0^2$ is a wave number for homogeneous matter and $E_{0j}$ is the field produced by the antenna number j.

An object may be described as a distribution of dielectrical permittivity in the volume.

A receiver antenna records the signal, which reflects both incident and scattered fields.

In order to solve the equation (4) we need to use some boundary conditions on the bound of a calculation domain. We are using nonreflecting boundary conditions on the domain bounds. An interaction of the electromagnetic fields with antennae is solved as a separate problem.

Antenna modeling. In practical applications, the value of incident fields is the important part of a reconstruction algorithm. Using the FDTD method we have found that for a rectangular waveguide transmitter (of an optional antenna type), the field distribution can be described as the vector Kirchhoff integral with a cosine distribution of electric field on the edge of the antenna:

$$E(r) = \iint [(n' \times E(r')) \times \nabla'G + (n' \cdot E)\nabla'G]ds' \quad (5)$$

where the Green function is:

$$G = \frac{\exp(ik_0 r)}{4\pi r}$$

$$E_z(r') = E_0 \cos(\pi y/a)$$

The equation (5) shows good agreement with the experimental results. The same type of antenna may be used as a receiver. To describe the process of a signal recording we use the reciprocity principle. It could provide different expressions for recorded signal. We use two of them in our calculations. First:

$$S_{ij} = C_1 \iiint_V E_i(r)E_j(r)\Delta\varepsilon(r)d^3r \quad (6)$$

where $S_{ij}$ is the signal received by antenna number i in the situation where antenna number j works as a transmitter or source, $C_1$ is a constant, $E_i$ is an electrical field distribution produced by the detecting antenna, $E_j$ is an electrical field distribution produced by the source antenna, $\Delta\epsilon$ is dielectrical permittivity distribution in the object, and the integral is taken in the domain V where the object is located. The equation (6) is used in the inverse problem solution.

$$S_{ij} = C_2 \oint \int_s [E_i \times H_j - E_j \times H_i]ds \quad (7)$$

where the integral is taken over the surface of the domain.

Direct problem solver. In order to solve direct problems we use a conjugate gradient method with a preconditioner. In order to do that, equation (4) should be rewritten in the form:

$$\hat{A}E_s = \nabla^2 E_s + k_{av}^2 E_s - graddivE_w = (k_{av}^2 - k^2)E_s + (k_0^2 - k^2)E_0 \quad (8)$$

where $k_{av}$ is an average value of k. The preconditioner operator can be constructed as a first step of the iterative process:

$$\hat{A}E_s^{n+1} = (k_{av}^2 - k^2)E_s^n + (k_0^2 - k^2)E_0 \quad (9)$$

Taking into account the fact that the left side of equation (8) is an expression with constant coefficient, (9) can be solved at step 1575 using sine-type Fourier transform for the case with zero boundary conditions on the bound of calculation domain. Then R. A. James's method (originally invented for static problems, but subsequently developed for electromagnetic problems) is applied to make boundary conditions nonreflected. This technique creates a very robust and effective method. Computational experiments show that the iterative process appears to work with any reasonable contrasts and provides nonreflecting conditions with very high accuracy. Using a sine-type Fourier transform at step 1575 can make calculations 8 times faster than with the regular Fourier approach.

FIG. 15A is a flow diagram of the direct problem solver portion 1535 of the image reconstruction process. The direct solver 1535 is used only for inverse problem solving. The input data in this case is the dielectric properties distribution in the form of a 3D array, which is received at step 1560. For the first step of the iteration, this input data is received from external input, while in subsequent iterations it is received from the previous iteration. Next to occur, at step 1565, is the preparation of the parameters and arrays, which do not change during the direct problem solving process: the wave number, the computational grids, and the Green function for the uniform space. After that, the iterative procedure of the conjugate gradients takes place at steps 1570–1580. First, the source member of equation (4) is calculated at step 1570. Then, every step of the conjugate gradient method requires fast Fourier transforms of the source functions, as shown at step 1575. In order to stop iterations the convergence of the process is checked at step 1580. Once the iterative procedure is finished, the non-reflecting boundary conditions have to be implemented at step 1585. Finally, the output of the process 1535 is created at step 1590. The output comprises arrays containing the electric fields inside of the computational domain and signals on the receivers for all transmitter positions.

Inverse problem solver. In order to solve the inverse problem in microwave tomography we apply the gradient method. In the case of a three-dimensional vector in cylindrical geometry this method needs significant modifications when compared with two dimensional and scalar cases. In general the inverse problem in EM field tomography can be formulated as a minimization problem:

$$J[\varepsilon] = \sum_{i,j} |S_{ij}^{theor} - S_{ij}^{exper}|^2 + \alpha\Omega[\varepsilon] \quad (10)$$

where $S_{ij}^{theor}$ are the theoretical values of the signal, $S_{ij}^{exper}$ are experimental values of the signal, and the last term is the Tichonov's regularization functional.

The key point of any minimization procedure is the method of a gradient calculation. It was proven that the gradient of functional in our case is:

$$J'[\varepsilon] = \sum_{ij} (E_j G_{ij}) * (S_{ij}^{theor} - S_{ij}^{exper}) + \alpha\Omega' \quad (11)$$

where $E_j$ and $G_{ij}$ are solutions of the following equations:

$$\nabla^2 E_j + k^2 E_j - \nabla(\nabla E_j) = F_j \quad (12)$$

$$\nabla^2 G_{ij} + k^2 G_{ij} - \nabla(\nabla G_{ij}) = P_{ij} \quad (13)$$

Functions $F_j$ and $P_{ij}$ describe the field patterns for antennae 48 being used as sources and detectors, respectively.

Direct computation using the equation (11) is very time consuming even in the 2D case and cannot be effectively applied in the 3D case. The reason is that every step requires N×M number of direct problems to be solved, where N is the number of transmitters, and M is the number of receivers. It was shown in our previous "scalar" work, and can be generalized in the vector case, that the function $$Z_j = \sum_i G_{ij}(S_{ij}^{theor} - S_{ij}^{exper})^* \quad (14)$$

can be the solution of the following equation:

$$\nabla^2 Z_j + k^2 Z_j - \nabla(\nabla Z_j) = \sum_i P_{ij}(S_{ij}^{theor} - S_{ij}^{exper}) \quad (15)$$

This makes it necessary to solve only two direct problems on each iterative step.

The calculation of the sum in the right side of equation (15) continues to be a difficult problem, because it requires summation on all receivers for all cells of the computational mesh. In order to overcome this obstacle, a two-step procedure may be applied. First, the following may be calculated on the surface of the computational domain:

$$Z_j^0 = \sum_i P_{ij}(S_{ij}^{theor} - S_{ij}^{exper}) \quad (16)$$

This needs significantly less computational effort compared to the calculation of the right part of equation (15). Second, the following equation may be solved with those boundary conditions:

$$\nabla^2 Z_j^0 + k_0^2 Z_j^0 = 0 \quad (17)$$

Equation (17) is the equation with constant coefficients and can be easily solved using sine-type FFT.

Finally, one step of the gradient method procedure requires solving two direct problems (equations (12) and (15)) plus one equation (equation (17)) with constant coefficients. In general this procedure looks to be the fastest known in literature.

One step of the iterative procedure can be implemented as:

$$\epsilon^{n=1} = \epsilon^n - J'[\epsilon^n]s \qquad (18)$$

where an iterative step is chosen in a trial method. The limitations on the upper and lower bounds of the values of the dielectric properties and the values of the dielectric properties on the bound of the object are applied in this step.

FIG. 15B is a flow diagram of the inverse problem solver portion 1500 of the image reconstruction process. At step 1505, the input data is received. The input data for the inverse problem solver 1500 includes physical and geometrical parameters of the computational process: the sixes of the computational domain, the working frequency, the maximum number of iterations and the signals from the antennae 48. Next to occur, at step 1510, is the preparation of the parameters and arrays, which do not change during the inverse problem solving iteration process: the wave number, the computational grids, and the Green function for the uniform space. After that, the iterative procedure of calculating the gradient of the residual function (equation (11)) itself takes place at steps 1515–1520, including the gradient calculation process itself at step 1515. In order to stop iterations the convergence of the process is checked at step 1520. This involves comparing the value of the residual error with the estimated experimental error. Once the iterative procedure is finished, the non-reflecting boundary conditions have to be implemented at step 1525. Finally, the output of the process 1500 is created at step 1530. The output comprises the dielectric properties distribution in the form of a 3D array.

FIG. 15C is a flow diagram of the gradient calculation portion 1515 of the image reconstruction process. The direct wave is calculated at step 1535 according to equation (12), followed at step 1540 by the calculation according to equation (16) of the source for back-propagating wave on the bounds of the computational domain. Then, at step 1545, the source of the back-propagating wave is calculated in the volume of the computational domain according to equation (17), and the back-propagating wave is calculated by solving equation (13) at step 1550. Finally, the gradient is calculated according to equation (11) at step 1555.

The image reconstruction algorithm of this invention includes a number of benefits. For example, using the nonreflecting boundary conditions plus sine-type FFT makes the direct problem solver of the invention the most effective one. Further, the proposed way to calculate the so-called back wave (equations (15), (16), (17)) allows working in real 3D multi antenna configuration. In addition, the method of signal calculation (equation (7)) is distinguished from any others and allows simulating the work of each antenna with high precision, and the mathematical algorithm itself is essentially parallel, which is particularly advantageous for parallel computing.

Figure 16:
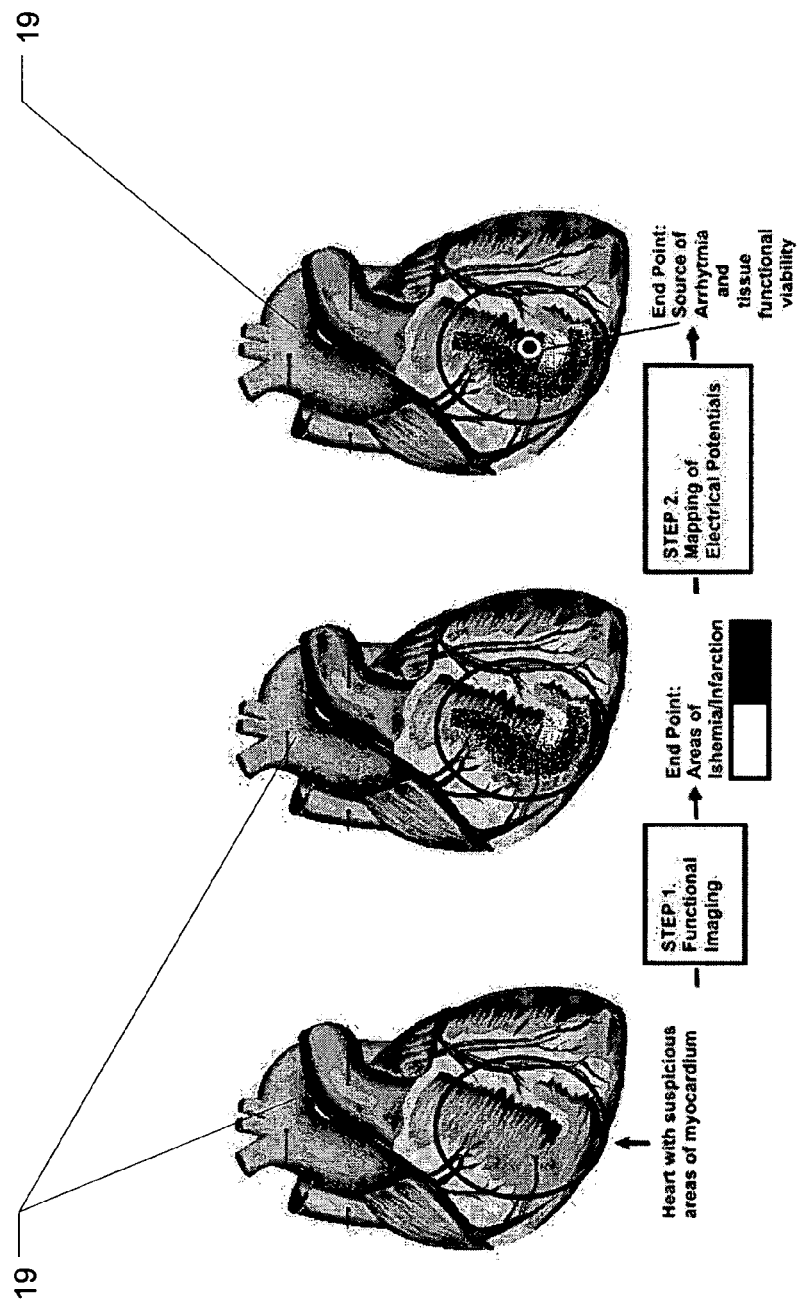
FIG. 16 is an illustration of an exemplary application of functional and electrical potential mapping according to a method of the present invention.

FIG. 16 is an illustration of an exemplary application of functional and electrical potential mapping according to a method of the present invention. As disclosed above, the invented system and method allows for both functional imaging of biological objects 19 and mapping of electrical excitation of biological tissues 19. This unique feature of the invention can be achieved as a two-step imaging process, as illustrated in FIG. 16. First, the system 10 is used as an electromagnetic tomographic spectroscopy tool for non-invasive assessment of functional and pathological conditions of a biological object 19 and the location of any areas of diseased tissues 19. For example, in FIG. 16, cardiac tissue with suspicious areas of myocardium is functionally imaged in Step 1 to identify areas of ischemia/infarction. Second, if the location of a diseased target is within a biologically excited tissue 19 (such as cardiac tissue, nervous tissue, musculoskeletal tissue, or the like), then a dielectrical contrast (sensitive) substance (solution) may be injected into the tissue (circulation system), thus allowing for non-invasive mapping of electrical excitation and the location of a source of irregularity (arrhythmogenety). Since the functional/pathological condition of the tissue in and near this source is known from the first step of the EM field imaging, it allows for unique and extremely valuable information to be developed for use in determining tissue viability and in choosing a strategy of further treatment and therapy. For example, in FIG. 16, electrical potentials in the areas of ischemia/infarction in the cardiac tissue are mapped to identify possible sources of arrhythmia and tissue functional viability. Further, if an ablation of this tissue is chosen than the same system can be used and electromagnetic energy can be focused precisely into the target area according to known techniques such as those described in the aforementioned U.S. Pat. Nos. 5,715,819, 6,026,173 and 6,333,087.

Of course, it should be apparent that it may not be necessary for the first step to be conducted at all. For example, other, more conventional, tests or diagnostic tools may alternatively be utilized to identify a particular tissue or area of tissue that are believed to warrant closer study. The second step described above may obviously be used to map the electrical excitation of the tissue and to isolate irregularities in the manner described herein.

The invention uses multimodality EM field: multi-frequency as well as multi-polarization with special timely fashion, synchronized with a biological electrical signal. This allows for both a more efficient and accurate image reconstruction algorithm and a combination of imaging and tissue spectroscopy for better assessment of tissue viability. The code-division technology may be used to distinguish each particular EM field source antennae from a plurality of simultaneously operating antennae. The multi-frequency EM field is preferably within a frequency range of about 50 KHz to 10 GHz and may be organized in a number of clusters (M) with N closer frequencies in each frequency cluster. In this case, using N close frequencies (with differences in about 10 MHz) allows for more effective images reconstruction having almost frequency independent tissue dielectrical properties. Since the reconstruction algorithm described above deals with so-called scattered EM field it requires measurements of the distribution of EM field in the working chamber 12 filled with a matching solution 17 but without an object 19—i.e., a so called "empty" field. This multi-frequency pack of radiation (N close frequencies) may be used instead of additional measurements of an "empty" field within the working chamber 12. This helps to solve stability problem of the system 10 and, finally, to improve reconstructed images. The M frequency clusters varied significantly (about or more than 50–100 MHz) are needed for tissue spectroscopy purposes.

In a further feature of the present invention, the functional viability of blood vessels may be assessed by introducing into the circulation system of the biological tissue, through injection or otherwise, a dielectrical contrast solution that is characterized by having dielectrical properties significantly different from those of the blood normally carried by the blood vessels. The system and methods described above may then be applied. Using code-division technology the total data acquisition time of the system is decreased to 5–10 msec. Clinically-proven iodine-based radiopaque agents, including but not limited to diatrzoate meglumine, or intralipid or other solutions and their mixtures may be used for this purpose.

Based on the foregoing information, it is readily understood by those persons skilled in the art that the present invention is susceptible of broad utility and application. Many embodiments and adaptations of the present invention other than those specifically described herein, as well as many variations, modifications, and equivalent arrangements, will be apparent from or reasonably suggested by the present invention and the foregoing descriptions thereof, without departing from the substance or scope of the present invention. Accordingly, while the present invention has been described herein in detail in relation to its preferred embodiment, it is to be understood that this disclosure is only illustrative and exemplary of the present invention and is made merely for the purpose of providing a full and enabling disclosure of the invention. The foregoing disclosure is not intended to be construed: to limit the present invention or otherwise exclude any such other embodiments, adaptations, variations, modifications or equivalent arrangements; the present invention being limited only by the claims appended hereto and the equivalents thereof. Although specific terms are employed herein, they are used in a generic and descriptive sense only and not for the purpose of limitation.

What is claimed is:

1. A method for non-destructive functional imaging and mapping of electrical excitation of biological objects, the method comprising:
    providing a plurality of electromagnetic field sources for generating an electromagnetic field domain in a target area;
    providing a plurality of electromagnetic field detectors for detecting at least a portion of the electromagnetic field domain in the target area;
    positioning a biological object within the target area;
    introducing, into the biological object, a sensitive material characterized by having a dielectrical property that is a function of the electrical field generated by the biological object;
    generating an electromagnetic field domain via a selected plurality of the electromagnetic field sources;
    selectively characterizing the electromagnetic field generated by each electromagnetic field source so that each of a selected plurality of electromagnetic field detectors recognizes a source of electromagnetic field from a plurality of electromagnetic field sources;
    controlling the electromagnetic field sources and the electromagnetic field detectors, so that electromagnetic fields generated by the selected plurality of electromagnetic field sources are received by the selected plurality of the electromagnetic field detectors after interacting with the biological object;
    based upon the electromagnetic field received at each electromagnetic field detector, measuring interference characteristics of an electromagnetic field caused by an electrical/dielectrical object and by an electromagnetic field generated by the biological object;
    determining an image of the biological object and the spread of electrical excitation in the biological object by inversing the electromagnetic fields detected by the plurality of electromagnetic field detectors; and
    displaying the spread of electrical excitation by excitation imaging means.

2. The method of claim 1, further comprising the step of:
    synchronizing the generating step with an electrical signal representative of an electrical excitation of the biological object.

3. The method of claim 2, wherein the biological object in the positioning, introducing, controlling, measuring, inversing and displaying steps is biological tissue.

4. The method of claim 3, wherein the biological tissue in the positioning, introducing, controlling, measuring, inversing and displaying steps is cardiac tissue.

5. The method of claim 4, wherein the electrical signal in the synchronizing step is an electrical signal representative of an electrical excitation of the cardiac tissue.

6. The method of claim 5, wherein the electrical signal is an electrocardiogram.

7. The method of claim 3, wherein the biological tissue in the positioning, introducing, controlling, measuring, inversing and displaying steps is nervous tissue.

8. The method of claim 7, wherein the electrical signal in the synchronizing step is an electrical signal representative of an electrical excitation of the nervous tissue.

9. The method of claim 3, wherein the biological tissue in the positioning, introducing, controlling, measuring, inversing and displaying steps is musculoskeletal tissue.

10. The method of claim 9, wherein the electrical signal in the synchronizing step is an electrical signal representative of an electrical excitation of the musculoskeletal tissue.

11. The method of claim 3, further comprising:
    displaying, by functional imaging means, areas of particular functional and pathological conditions of the biological tissue.

12. The method of claim 11, wherein the particular functional and pathological conditions of the biological tissue include at least one of tissue blood content, ischemia, infraction, hypoxia, malignancies, benign tumor, edema, and temperature.

13. The method of claim 2, wherein the providing steps include providing a plurality of integrated electromagnetic field source-detectors for generating an electromagnetic field domain in a target area and detecting at least a portion of the electromagnetic field domain in the target area.

14. The method of claim 2, wherein the electromagnetic field domain is a multiple modality electromagnetic field domain.

15. The method of claim 14, wherein the generating step includes generating a multiple modality electromagnetic field domain formed from electromagnetic fields in a frequency range of about 50 KHz to 10 GHz.

16. The method of claim 15, wherein the generating step includes generating multiple modality electromagnetic field domain formed from electromagnetic fields with multiple polarizations.

17. The method of claim 16, wherein the multiple polarizations in the generating step are linear within multiple directions in the three-dimensional space.

18. The method of claim 16, wherein the multiple polarizations in the generating step are elliptical within multiple directions in the three-dimensional space.

19. The method of claim 15, wherein the electromagnetic fields in the generating step are organized into frequency clusters with a predetermined number of closer frequencies in each frequency cluster.

20. The method of claim 2, wherein the sensitive material in the introducing step is a multiple component media that includes ferroelectric grains of different sizes ranging from 0.5–100 μm.

21. The method of claim 20, wherein at least some of the ferroelectric grains in the introducing step are formed from barium modified strontium titanium oxide.

22. The method of claim 20, wherein the ferroelectric grains in the introducing step have different shapes, including spheres, ellipsoids and cylinders.

23. The method of claim 2, wherein the sensitive material in the introducing step is a multiple component media that includes potentiometric liquid crystals.

24. The method of claim 23, wherein the potentiometric liquid crystals in the introducing step include MBBA, 7CB.

25. The method of claim 2, wherein the sensitive material in the introducing step is a multiple component media includes a potentiometric dye.

26. The method of claim 25, wherein the potentiometric dye in the introducing step includes at least one of merocyanine, rhodamine, cyanine, oxonol or naphthyl styryl.

27. The method of claim 2, wherein the displaying step includes displaying at least one source of arrhythmogeneties in the electrical excitation process.

28. The method of claim 2, wherein the introducing step includes injecting the sensitive material into the biological tissue.

29. A system for non-destructive functional imaging and mapping of electrical excitation of biological tissues, the system comprising:
a plurality of electromagnetic field source for generating an electromagnetic field domain in a target area;
a plurality of electromagnetic field detectors for detecting at least a portion of the electromagnetic field domain in the target area;
a working chamber for positioning a biological tissue within the target area;
a sensitive material, introduced into the biological tissue, that is characterized by having a dielectrical property that is a function of the electrical field that is generated by the biological tissue;
a controller, operably coupled to the plurality of electromagnetic field sources and the electromagnetic field detectors to cause electromagnetic fields generated by a selected plurality of the electromagnetic field sources to be received by a selected plurality of the electromagnetic field detectors after interacting with the biological tissue;
a module for measuring interference characteristics of the electromagnetic field caused by an electrical/dielectrical object and by the electromagnetic field generated by the biological tissue;
an imaging computer for determining an image of the biological tissue and the spread of electrical excitation in the biological tissue by inversing the electromagnetic fields detected by the plurality of electromagnetic field detectors; and
a graphical display for displaying at least one image representative of the spread of electrical excitation in the biological tissue.

30. The system of claim 29, further comprising a reference module for synchronizing the generation of electromagnetic fields with an electrical signal representative of an electrical excitation of the biological tissue.

31. The system of claim 30, wherein the biological tissue is cardiac tissue, and wherein the generation of electromagnetic fields is synchronized with an electrical signal representative of an electrical excitation of the cardiac tissue.

32. The system of claim 31, wherein the electrical signal is an electrocardiogram.

33. The system of claim 30, wherein the biological tissue is nervous tissue, and wherein the generation of electromagnetic fields is synchronized with an electrical signal representative of an electrical excitation of the nervous tissue.

34. The system of claim 30, wherein the biological tissue is musculoskeletal tissue, and wherein the generation of electromagnetic fields is synchronized with an electrical signal representative of an electrical excitation of musculoskeletal tissue.

35. The system of claim 30, wherein the graphical display includes at least one image, of a particular functional or pathological condition of the biological tissue, on which the at least one image representative of the spread of electrical excitation in the biological tissue is overlaid.

36. The system of claim 35, wherein the at least one image or a particular functional or pathological condition of the biological tissue includes an image of at least one of tissue blood content, ischemia, infraction, hypoxia, malignancies, benign tumor, edema, and temperature.

37. The system of claim 30, wherein each electromagnetic field source is integrated with an electromagnetic field detector in a single module.

38. The system of claim 30, wherein the electromagnetic field domain is a multiple modality electromagnetic field domain.

39. The system of claim 38, wherein the multiple modality electromagnetic field domain is formed from electromagnetic fields in a frequency range of about 50 KHz to 10 GHz.

40. The system of claim 39, wherein the multiple modality electromagnetic field domain is formed from electromagnetic fields with multiple polarizations.

41. The system of claim 40, wherein the multiple polarizations of the electromagnetic fields are linear within multiple directions in the three-dimensional space.

42. The system of claim 40, wherein the multiple polarizations of the electromagnetic fields are elliptical within multiple directions in the three-dimensional space.

43. The system of claim 39, wherein the electromagnetic fields in multiple modality electromagnetic field domain are organized into frequency clusters with a predetermined number of closer frequencies in each frequency cluster.

44. The system of claim 30, wherein the sensitive material is a multiple component media that includes ferroelectric grains of different sizes ranging from 0.5–100 μm.

45. The system of claim 44, wherein at least some of the ferroelectric grains are formed from barium modified strontium titanium oxide.

46. The system of claim 44, wherein the ferroelectric grains have different shapes, including spheres, ellipsoids and cylinders.

47. The system of claim 30, wherein the sensitive material is a multiple component media that includes potentiometric liquid crystals.

48. The system of claim 47, wherein the potentiometric liquid crystals include MBBA, 7CB.

49. The system of claim 30, wherein the sensitive material is a multiple component media includes a potentiometric dye.

50. The system of claim 49, wherein the potentiometric dye includes at least one of merocyanine, rhodamine, cyanine, oxonol or naphthyl styryl.

51. A method for non-destructive functional imaging of biological objects, blood vessels in the biological objects and mapping of electrical excitation of the biological objects, the method comprising:
- providing a plurality of electromagnetic field sources for generating an electromagnetic field domain in a target area;
- providing a plurality of electromagnetic field detectors for detecting at least a portion of the electromagnetic field domain in the target area;
- positioning a biological object within the target area;
- introducing into a circulation system a dielectrical contrast solution, characterized by having dielectrical properties significantly different from those of blood;
- generating an electromagnetic field domain via a selected plurality of the electromagnetic field sources;
- selectively characterizing the electromagnetic field generated by each electromagnetic field source so that each of a selected plurality of electromagnetic field detectors recognizes a source of electromagnetic field from a plurality of electromagnetic field sources;
- controlling the electromagnetic field sources and the electromagnetic field detectors, so that electromagnetic fields generated by the selected plurality of electromagnetic field sources are received by the selected plurality of the electromagnetic field detectors after interacting with the biological object;
- based upon the electromagnetic field received at each electromagnetic field detector, measuring interference characteristics of an electromagnetic field caused by an electrical/dielectrical object and by an electromagnetic field generated by the biological object;
- determining an image of the biological object and the spread of electrical excitation in the biological object by inversing the electromagnetic fields detected by the plurality of electromagnetic field detectors; and
- displaying the spread of electrical excitation by excitation imaging means.

52. The method of claim 51, further comprising the step of:
- introducing, into the biological object, a sensitive material characterized by having a dielectrical property that is a function of the electrical field generated by the biological object.

53. The method of claim 52, wherein the dielectrical contrast material introduced into the circulation system is an iodine based radiopaque agent.

54. The method of claim 53, wherein the iodine-based radiopaque agent introduced into the circulation system is diatrzoate meglumine.

55. The method of claim 52, wherein the dielectrical contrast material introduced into the circulation system is an intralipid solution.

56. A system for non-destructive functional imaging and mapping of electrical excitation of biological tissues, the system comprising:
- a plurality of electromagnetic field source for generating an electromagnetic field domain in a target area;
- a plurality of electromagnetic field detectors for detecting at least a portion of the electromagnetic field domain in the target area;
- a working chamber for positioning a biological tissue within the target area;
- a dielectrical contrast solution, introduced into the circulation system, that is characterized by having dielectrical properties significantly different from those of blood;
- a controller, operably coupled to the plurality of electromagnetic field sources and the electromagnetic field detectors to cause electromagnetic fields generated by a selected plurality of the electromagnetic field sources to be received by a selected plurality of the electromagnetic field detectors after interacting with the biological tissue;
- a module for measuring interference characteristics of the electromagnetic field caused by an electrical/dielectrical object and by the electromagnetic field generated by the biological tissue;
- an imaging computer for determining an image of the biological tissue and the spread of electrical excitation in the biological tissue by inversing the electromagnetic fields detected by the plurality of electromagnetic field detectors; and
- a graphical display for displaying at least one image representative of the spread of electrical excitation in the biological tissue.

57. The method of claim 56, further comprising a sensitive material, introduced into the biological tissue, that is characterized by having a dielectrical property that is a function of the electrical field that is generated by the biological tissue.

58. The method of claim 57, wherein the dielectrical contrast material is an iodine based radiopaque agent.

59. The method of claim 58, wherein the iodine-based radiopaque agent is diatrzoate meglumine.

60. The method of claim 57, wherein the dielectrical contrast material is an intralipid solution.

61. A method for non-destructive functional imaging of biological objects, the method comprising:
- providing a plurality of electromagnetic field sources;
- providing a plurality of electromagnetic field detectors;
- generating electromagnetic fields, in the absence of a biological object, via the plurality of the electromagnetic field sources;
- measuring the generated electromagnetic fields in the absence of a biological object;
- generating electromagnetic fields, in the presence of a biological object, via the plurality of the electromagnetic field sources;
- controlling the electromagnetic field sources and the electromagnetic field detectors, so that electromagnetic fields generated by the plurality of electromagnetic field sources are received by the selected plurality of the electromagnetic field detectors after interacting with the biological object; and
- imaging the biological object using a signal inversion process, the signal inversion process including:
  - (a) executing a calibration procedure which permits detected electromagnetic fields to be compared with electromagnetic fields measured in the absence of a biological object, the procedure including selecting a electromagnetic fields source and a plurality of electromagnetic fields detectors used in the procedure and calculating the calibration signals for both measured and calculated data sets and division both sets of data on consequent calibrated constants;
  - (b) calculating a gradient of a functional in order to calculate one step of an iterative procedure, the calculating step including the substeps of:
    - (i) modeling an incident field for each source and detector of electromagnetic fields,
    - (ii) solving a direct problem for each source of electromagnetic fields, (iii) calculating a back wave on the bounds of computational domain for each source of electromagnetic fields, and
(iv) calculating a back wave inside the computational domain,
wherein the gradient of the functional calculation by combining the direct and back waves for all sources of the electromagnetic fields;
(c) iteratively calculating the absolute value of the functional divided by the absolute value of the gradient and multiplied by an empiric constant to produce the iterative step for the calculation of the changing dielectric properties; and
(d) accepting or declining the current step changing the dielectric properties depending on the functional, wherein:
(i) if the functional decreases during the current step, accepting the current step changing the dielectric properties; and
(ii) if the functional does not decrease during the current step, declining the current step changing the dielectric properties
wherein the iterative procedure is successful if the functional achieved the threshold value which corresponds with measuring noise level and statistics and is unsuccessful if the functional does not achieve the threshold after a predetermined number of iterations.

62. A method for non-destructive functional imaging of biological objects, the method comprising:
providing a plurality of electromagnetic field sources;
providing a plurality of electromagnetic field detectors;
generating electromagnetic fields, in the absence of a biological object, via the plurality of the electromagnetic field sources;
measuring the generated electromagnetic fields in the absence of a biological object;
generating electromagnetic fields, in the presence of a biological object, via the plurality of the electromagnetic field sources;
controlling the electromagnetic field sources and the electromagnetic field detectors, so that electromagnetic fields generated by the plurality of electromagnetic field sources are received by the selected plurality of the electromagnetic field detectors after interacting with the biological object; and
imaging the biological object using a direct problem solver that serves to solve Maxwell's equations in parallel with the nonreflecting boundary conditions, the direct problem solver including:
calculating a source function that is the physical source of electromagnetic fields modeling and calculating its value on a computational mesh;
determining numerical values of the three-dimensional (3D) Green's function calculations;
performing a direct 3D discrete sine Fourier transform on the source function;
performing a boundary conditions correction that introduces real nonreflecting boundary conditions instead of zero value boundary conditions which appear as a results of the sine Fourier transform application;
applying the 3D Fourier image of the Green's function to the solution which gives the problem solving in the discrete Fourier space; and
performing the 3D inverse sine Fourier transform which solves the problem in the real physical space.

63. A method for non-destructive functional imaging of biological objects, the method comprising:
providing a plurality of electromagnetic field sources;
providing a plurality of electromagnetic field detectors;
generating electromagnetic fields, in the absence of a biological object, via the plurality of the electromagnetic field sources;
measuring the generated electromagnetic fields in the absence of a biological object;
generating electromagnetic fields, in the presence of a biological object, via the plurality of the electromagnetic field sources;
controlling the electromagnetic field sources and the electromagnetic field detectors, so that electromagnetic fields generated by the plurality of electromagnetic field sources are received by the selected plurality of the electromagnetic field detectors after interacting with the biological object; and
imaging the biological object using a computational process that includes a back wave calculation procedure for solving Maxwell's equations for the waves propagating from the area of plurality of electromagnetic field detectors of and having an amplitude corresponding to the difference between the values in the presence and the absence of the biological object, the computational process including:
the fast procedure of waves propagating through the free space starting in the detectors area and finishing on the computational domain bounds;
the fast procedure of waves propagating through free space with boundary conditions of the first order using the sine type fast Fourier transform; and
the fast procedure of waves propagating through inhomogeneous matter with unreflecting boundary conditions utilizing a direct problem solver.

* * * * *